(12) United States Patent
Lambrecht et al.

(10) Patent No.: US 8,591,574 B2
(45) Date of Patent: Nov. 26, 2013

(54) CARDIAC VALVE PROCEDURE METHODS AND DEVICES

(75) Inventors: Gregory H. Lambrecht, Natick, MA (US); John Liddicoat, Sewickley, PA (US); Robert Kevin Moore, Natick, MA (US)

(73) Assignee: Medtronic, Inc., Minneapolis, MN (US)

( * ) Notice: Subject to any disclaimer, the term of this patent is extended or adjusted under 35 U.S.C. 154(b) by 120 days.

(21) Appl. No.: 13/220,179

(22) Filed: Aug. 29, 2011

(65) Prior Publication Data

US 2011/0313446 A1   Dec. 22, 2011

Related U.S. Application Data

(63) Continuation of application No. 11/115,064, filed on Apr. 26, 2005, which is a continuation of application No. 09/700,167, filed as application No. PCT/US00/02126 on Jan. 27, 2000, now Pat. No. 6,896,690.

(60) Provisional application No. 60/161,934, filed on Oct. 28, 1999, provisional application No. 60/152,135, filed on Aug. 25, 1999, provisional application No. 60/117,599, filed on Jan. 27, 1999.

(51) Int. Cl.
*A61F 2/24* (2006.01)
*A61M 29/00* (2006.01)

(52) U.S. Cl.
USPC .............................. 623/2.1; 606/198; 606/200

(58) Field of Classification Search
CPC ............. A61F 2/01; A61F 2/013; A61F 2/24; A61F 2/2412
USPC ........ 623/1, 24–1.26, 2.1–2.19; 606/200, 108
See application file for complete search history.

(56) References Cited

U.S. PATENT DOCUMENTS

| 3,671,979 A | 6/1972 | Moulopoulos |
| 3,996,938 A | 12/1976 | Clark, III |
| 4,056,854 A | 11/1977 | Boretos et al. |

(Continued)

FOREIGN PATENT DOCUMENTS

| EP | 0408245 | 1/1991 |
| EP | 0850607 | 7/1998 |

(Continued)

OTHER PUBLICATIONS

Antonatos PG, et al., Effect of the positioning of a balloon valve in the aorta on coronary flow during aortic regurgitation, J Thorac Cardiovasc Surg; Jul. 1984;88(1):128-33.

(Continued)

*Primary Examiner* — Jason-Dennis Stewart

(57) ABSTRACT

A method of performing an endovascular procedure within a patient can include inserting a filter into the patient's vascular system to restrict the passage of emboli through the filter while allowing blood to flow through the filter. The method can also include inserting a prosthetic valve into the patient's vascular system in a compressed state, and advancing the prosthetic valve to a site of implantation upstream of the filter. Additionally, the method includes implanting the prosthetic valve at the site of implantation by expanding at least a portion of the prosthetic value, and removing the filter from the patient's vascular system.

34 Claims, 20 Drawing Sheets

(56) References Cited

U.S. PATENT DOCUMENTS

| | | | |
|---|---|---|---|
| 4,425,908 A | 1/1984 | Simon | |
| 4,527,549 A | 7/1985 | Gabbay | |
| 4,902,272 A | 2/1990 | Milder et al. | |
| 5,108,419 A | 4/1992 | Reger et al. | |
| 5,160,342 A | 11/1992 | Reger et al. | |
| 5,163,953 A * | 11/1992 | Vince | 623/2.11 |
| 5,254,097 A | 10/1993 | Schock et al. | |
| 5,300,086 A | 4/1994 | Gory et al. | |
| 5,324,304 A | 6/1994 | Rasmussen | |
| 5,329,942 A | 7/1994 | Gunther et al. | |
| 5,370,685 A | 12/1994 | Stevens | |
| 5,397,351 A | 3/1995 | Pavcnik et al. | |
| 5,411,552 A | 5/1995 | Andersen et al. | |
| 5,476,510 A | 12/1995 | Eberhardt et al. | |
| 5,509,428 A | 4/1996 | Dunlop | |
| 5,545,214 A | 8/1996 | Stevens | |
| 5,549,626 A | 8/1996 | Miller et al. | |
| 5,549,665 A | 8/1996 | Vesely et al. | |
| 5,554,185 A | 9/1996 | Block et al. | |
| 5,571,215 A | 11/1996 | Sterman et al. | |
| 5,584,879 A | 12/1996 | Reimold et al. | |
| 5,607,465 A | 3/1997 | Camilli | |
| 5,682,906 A | 11/1997 | Sterman et al. | |
| 5,702,368 A | 12/1997 | Stevens et al. | |
| 5,713,951 A | 2/1998 | Garrison et al. | |
| 5,716,370 A | 2/1998 | Williamson et al. | |
| 5,718,725 A | 2/1998 | Sterman et al. | |
| 5,728,153 A | 3/1998 | Menkis et al. | |
| 5,769,816 A | 6/1998 | Barbut et al. | |
| 5,797,960 A | 8/1998 | Stevens et al. | |
| 5,800,457 A | 9/1998 | Gelbfish | |
| 5,800,525 A | 9/1998 | Bachinski et al. | |
| 5,814,064 A | 9/1998 | Daniel et al. | |
| 5,814,097 A | 9/1998 | Sterman et al. | |
| 5,827,237 A | 10/1998 | Macoviak et al. | |
| 5,827,324 A | 10/1998 | Cassell et al. | |
| 5,840,081 A | 11/1998 | Andersen et al. | |
| 5,846,260 A | 12/1998 | Maahs | |
| 5,848,964 A | 12/1998 | Samuels | |
| 5,855,597 A | 1/1999 | Jayaraman | |
| 5,855,601 A * | 1/1999 | Bessler et al. | 623/2.38 |
| 5,876,367 A | 3/1999 | Kaganov et al. | |
| 5,893,869 A | 4/1999 | Barnhart et al. | |
| 5,910,154 A | 6/1999 | Tsugita et al. | |
| 5,911,734 A | 6/1999 | Tsugita et al. | |
| 5,916,193 A | 6/1999 | Stevens et al. | |
| 5,925,063 A | 7/1999 | Khosravi | |
| 5,928,261 A | 7/1999 | Ruiz | |
| 5,935,139 A | 8/1999 | Bates | |
| 5,941,896 A | 8/1999 | Kerr | |
| 5,947,995 A | 9/1999 | Samuels | |
| 5,954,741 A | 9/1999 | Fox | |
| 5,954,745 A | 9/1999 | Gertler et al. | |
| 5,957,949 A | 9/1999 | Leonhardt et al. | |
| 5,972,029 A | 10/1999 | Fuisz | |
| 5,972,030 A | 10/1999 | Garrison et al. | |
| 5,976,172 A | 11/1999 | Homsma et al. | |
| 5,980,555 A | 11/1999 | Barbut et al. | |
| 5,980,570 A | 11/1999 | Simpson | |
| 5,984,959 A | 11/1999 | Robertson et al. | |
| 5,989,281 A | 11/1999 | Barbut et al. | |
| 6,019,790 A | 2/2000 | Holmberg et al. | |
| 6,051,014 A | 4/2000 | Jang | |
| 6,066,158 A | 5/2000 | Engelson et al. | |
| 6,142,987 A | 11/2000 | Tsugita | |
| 6,146,396 A | 11/2000 | Konya et al. | |
| 6,179,859 B1 | 1/2001 | Bates et al. | |
| 6,235,045 B1 | 5/2001 | Barbut et al. | |
| 6,245,089 B1 | 6/2001 | Daniel et al. | |
| 6,258,120 B1 | 7/2001 | McKenzie et al. | |
| 6,287,321 B1 | 9/2001 | Jang | |
| 6,309,399 B1 | 10/2001 | Barbut et al. | |
| 6,325,815 B1 | 12/2001 | Kusleika et al. | |
| 6,334,869 B1 | 1/2002 | Leonhardt et al. | |
| 6,338,735 B1 | 1/2002 | Stevens | |
| 6,361,545 B1 | 3/2002 | Macoviak et al. | |
| 6,364,896 B1 | 4/2002 | Addis | |
| 6,371,970 B1 | 4/2002 | Khosravi et al. | |
| 6,375,670 B1 | 4/2002 | Greenhalgh | |
| 6,395,014 B1 | 5/2002 | Macoviak et al. | |
| 6,499,487 B1 | 12/2002 | McKenzie et al. | |
| 6,511,496 B1 | 1/2003 | Huter et al. | |
| 6,589,264 B1 | 7/2003 | Barbut et al. | |
| 6,692,513 B2 | 2/2004 | Streeter et al. | |
| 6,706,055 B2 | 3/2004 | Douk et al. | |
| 6,769,434 B2 | 8/2004 | Liddicoat et al. | |
| 6,890,330 B2 | 5/2005 | Streeter et al. | |
| 6,896,690 B1 | 5/2005 | Lambrecht et al. | |
| 6,929,653 B2 | 8/2005 | Streeter | |
| 6,994,718 B2 | 2/2006 | Groothuis et al. | |
| 7,011,672 B2 | 3/2006 | Barbut et al. | |
| 7,172,614 B2 | 2/2007 | Boyle et al. | |
| 7,176,614 B2 | 2/2007 | Lee et al. | |
| 2001/0041908 A1 | 11/2001 | Levinson et al. | |
| 2003/0176884 A1 | 9/2003 | Berrada et al. | |

FOREIGN PATENT DOCUMENTS

| | | |
|---|---|---|
| WO | WO 97/17100 | 5/1997 |
| WO | WO 99/15223 | 4/1999 |
| WO | WO 99/16382 | 4/1999 |
| WO | WO 99/22673 | 5/1999 |
| WO | WO 99/33414 | 7/1999 |
| WO | WO 00/44313 | 8/2000 |
| WO | WO 00/47139 | 8/2000 |
| WO | WO 01/45592 | 6/2001 |
| WO | WO 01/49215 | 7/2001 |
| WO | WO 01/80776 | 11/2001 |
| WO | WO 03/020171 A2 | 3/2003 |

OTHER PUBLICATIONS

Antonatos PG, et al, Intraventricular Pumping At the Mitral Ring in Mitral Regurgitation; Life Support Syst; 1985; 3 Suppl1 :167-71.

Antonatos PG, et al., The Use of a Small Intra-Aortic Balloon to Increase Coionary Flow; Life Support Syst; Jul.-Sep. 1983 1(3): 151-64.

Frederiksen J, et al., Use of a Counterpulsation Balloon as a Substitute for the Pulmonic Valve: A New Application; Ann Thorac Surg; Jun. 1986; 41(6): 616-21.

Matsubara T, et al., Balloon Catheter With Check Valves for Experimental Relief of Acute Aortic Regurgitation; Am Heart J; Oct. 1992; 124(4): 1002-8.

Moulopoulos SD, et al, Intra-Aortic Balloon Pump for Relief of Aortic Regurgitation. Experimental Study, J Thorac Cardiovasc Surg; Jul. 1980:80(1): 38-44.

Siwek LG, et al., Acutet Control of Pulmonary Regurgitation With a Balloon "Valve". An experimental investigation, J Thorac Cardiovasc Surg; Sep. 1985; 90(3): 404-9.

Cartwright RS, et al., Combined Replacement of Aortic and Mitral Valves; J.A.M.A., Apr. 7, 1962; 86-90.

Davidson, et al., "Percutaneous therapies for valvular heart disease," Cardiovascular Pathology 15 (2006) 123-129.

Lutter et al., "Percutaneous Valve Replacement: Current State and Future Prospects," Ann. Thorac. Sorg. 2004; 78:2199-2206.

\* cited by examiner

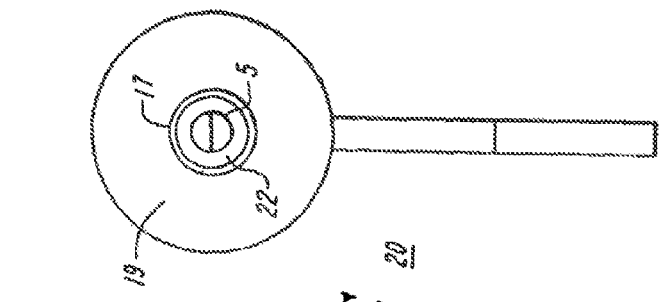
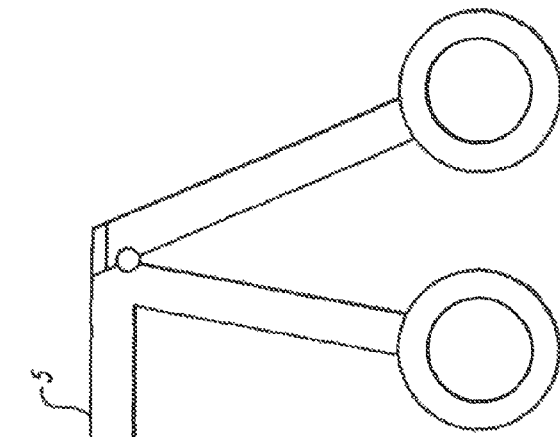
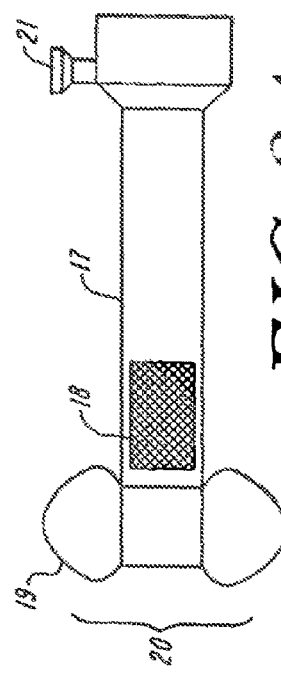
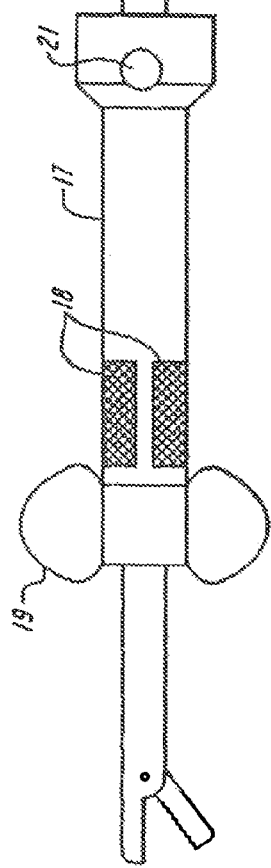
FIG. 2A
FIG. 2B
FIG. 2C

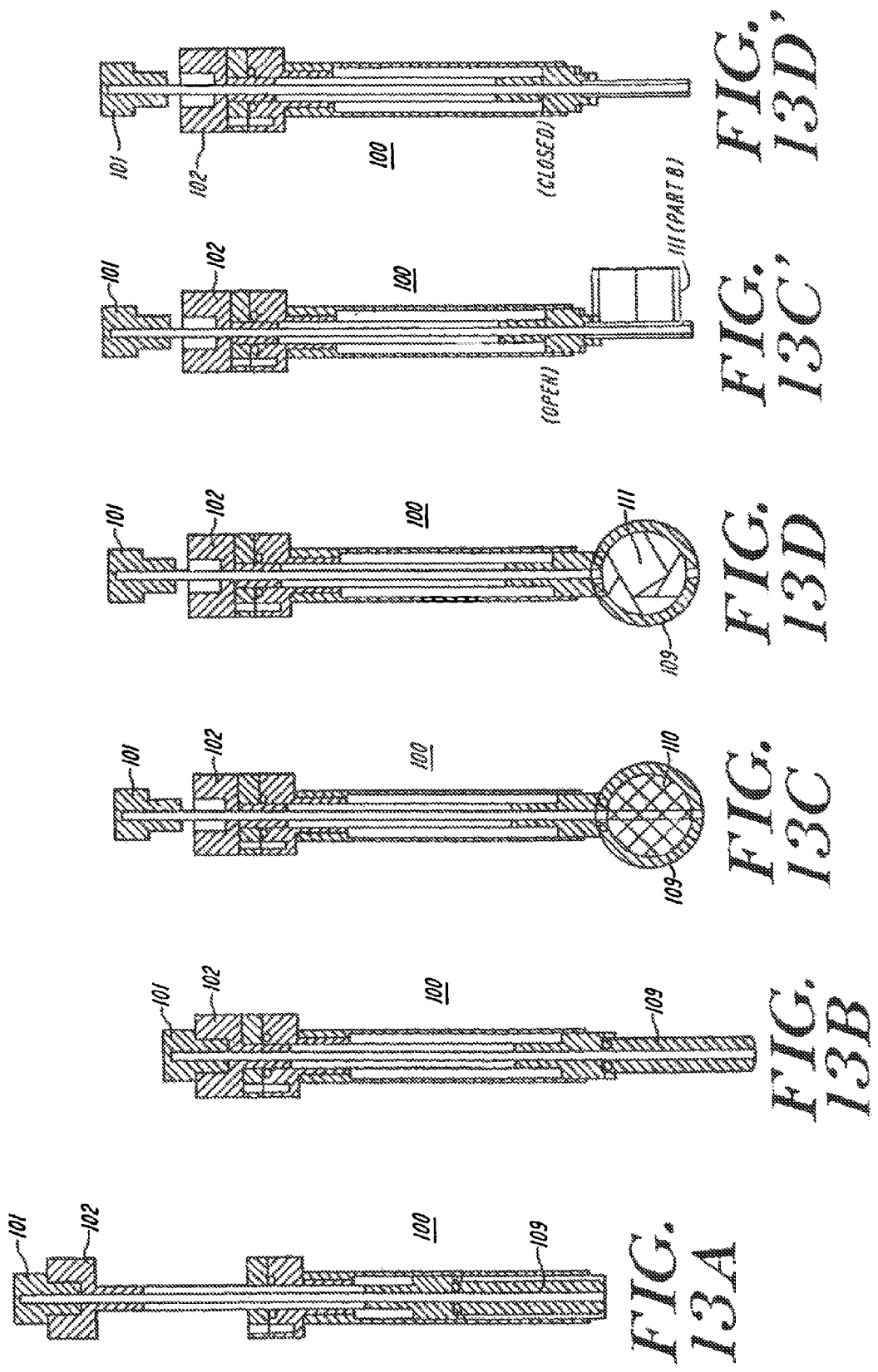

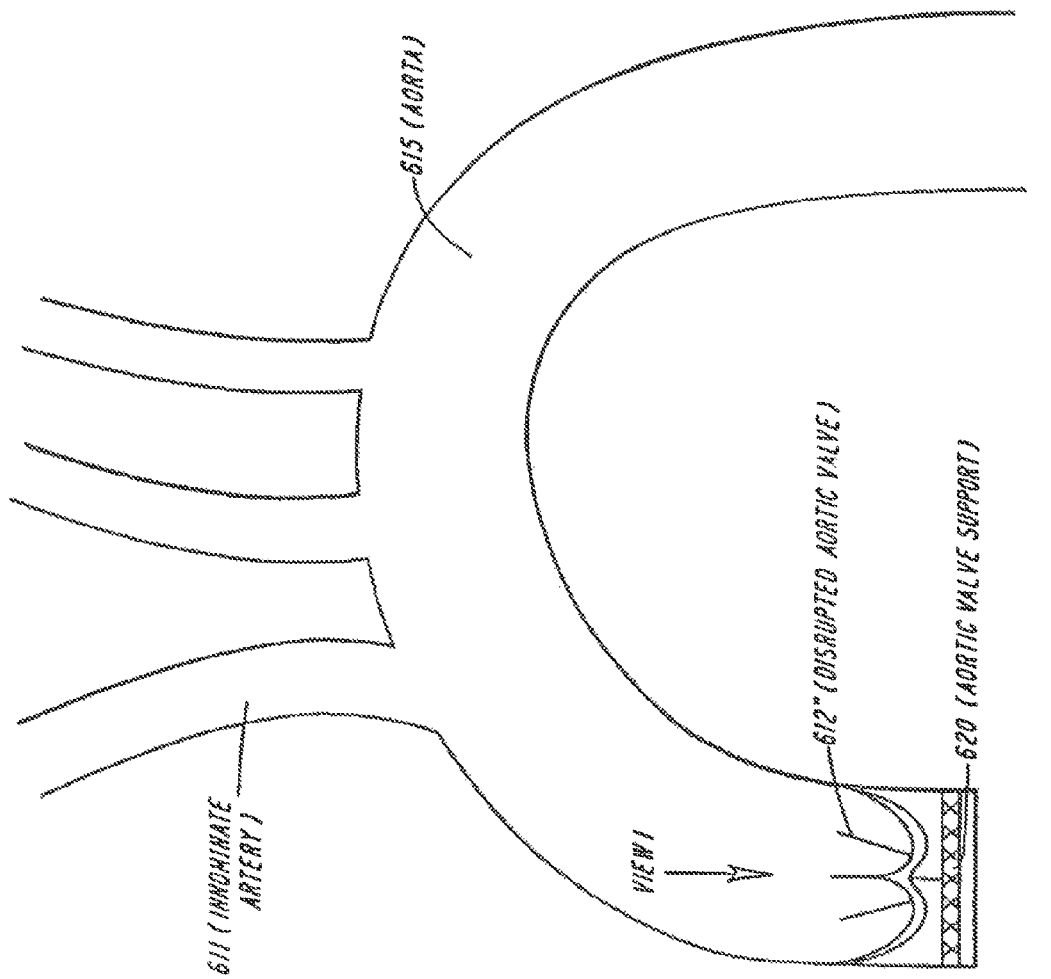
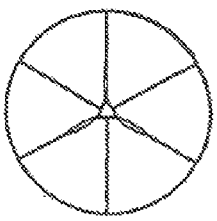
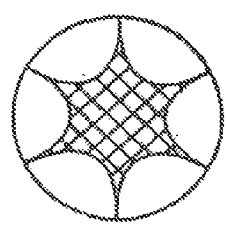
FIG. 23B

CARDIAC VALVE PROCEDURE METHODS AND DEVICES

CROSS-REFERENCE TO RELATED APPLICATIONS

This application is a continuation of U.S. Application Ser. No. 11/115,064, filed Apr. 26, 2005; which is a continuation of U.S. Application Ser. No. 09/700,167, filed Nov. 9, 2000, now U.S. Pat. No. 6,896,690, issued May 24, 2005; which is the U.S. national stage of international application No. PCT/US00/02126, filed Jan. 27, 2000; which claims the benefit of U.S. provisional applications Nos. 60/161,934, filed Oct. 28, 1999; 60/152,135, filed Aug. 25, 1999; and 60/117,599, filed Jan. 27, 1999.

BACKGROUND

Of all valvular heart lesions, aortic stenosis carries the worst prognosis. Within one year of diagnosis, half of patients with critical aortic stenosis have died, and by three years this figure rises to 80%. Currently, there is only one effective treatment for patients with aortic stenosis—aortic valve replacement via open heart surgery. Unfortunately, this is a substantial and invasive undertaking for the patient.

While there have been significant advances in heart valve technology over the last thirty years, there has been little progress in the development of safer and less invasive valve delivery systems. Aortic valve replacement currently requires a sternotomy or thoracotomy, use of cardiopulmonary bypass to arrest the heart and lungs, and a large incision on the aorta. The native valve is resected through this incision and a prosthetic valve is sutured to the inner surface of the aorta with a multitude of sutures passing into the wall of the aorta. This procedure is accompanied by a 5% mortality rate, in addition to significant morbidity (stroke, bleeding, myocardial infarction, respiratory insufficiency, wound infection) related to the use of cardiopulmonary bypass and the approach to the aortic valve. Elderly patients and those who require concomitant coronary artery bypass grafting experience increased morbidity and mortality. All patients require 4 to 6 weeks to recover from the procedure.

Less invasive approaches to aortic valve surgery have followed two paths. In the Eighties, there was a flurry of interest in percutaneous balloon valvotomy. In this procedure, a cardiologist introduced catheters through the femoral artery to dilate the patient's aortic valve, thereby relieving the stenosis. Using the technology available at that time, success was limited. The valve area was increased only minimally, and nearly all patients had restenosis within one year. More recently, surgeons have approached the aortic valve via smaller chest wall incisions. These approaches still require cardiopulmonary bypass and cardiac arrest, which entail significant morbidity and a prolonged postoperative recovery.

A truly minimally invasive approach to the treatment of aortic valve disease requires aortic valve replacement without cardiopulmonary bypass. Such an approach would reduce patient morbidity and mortality and hasten recovery. Although there has been great progress in the treatment of coronary artery disease without cardiopulmonary bypass (angioplasty/stenting and "off-pump" coronary artery bypass grafting), similar advances have not yet been realized in heart valve surgery. With an aging population and improved access to advanced diagnostic testing, the incidence of aortic stenosis will continue to increase. The development of a system for "off-pump" aortic valve replacement would be of tremendous benefit to this increasing patient population.

There are three significant challenges to replacing a diseased aortic valve without cardiopulmonary bypass. The first is to remove the valve without causing stroke or other ischemic events that might result from particulate material liberated while manipulating the valve. The second is to prevent cardiac failure during removal of the valve. The aortic valve serves an important function even when diseased. When the valve becomes acutely and severely incompetent during removal, the patient develops heart failure leading to death unless the function of the valve is taken over by another means. The third challenge is placing a prosthetic valve into the vascular system and affixing it to the wall of the aorta.

Temporary valves have been reported in the art, most notably by Boretos, et. al. in U.S. Pat. No. 4,056,854 and Moulopoulos in U.S. Pat. No. 3,671,979. All temporary valves disclosed to date have been inserted into a vessel, advanced to a location distant from the insertion site and then expanded radially from the center of the vessel.

These designs have many disadvantages. First, they tend to occupy a significant length of the vessel when deployed. During a valve procedure, it may be advantageous to place the temporary valve in a vessel between two branches leading from that vessel. It may also be necessary to insert other tools through the vessel wall between those two branches. A temporary valve such as the ones disclosed in the art may leave very little room between the branches for insertion of these tools. The valves disclosed to date tend also to be rather flimsy and may have difficulty supporting the fluid pressures while the valve is closed. A more significant disadvantage of these valves is that they generally must be inserted into a vessel at a significant distance from the valve to allow adequate room for deployment. If some portions of the operation are performed through the chest wall, insertion of such a temporary valve may require a separate incision distant from the chest cavity. This adds morbidity and complexity to the procedure. Another drawback of the prior art is that valves with three or fewer leaflets rely on the perfect performance of each of those leaflets. If one of the leaflets malfunctions, the valve fails to function adequately.

Throughout this disclosure the terms proximal and distal will be used to describe locations within the vascular anatomy. In the arterial system, proximal means toward the heart while distal means away from the heart. In the venous system, proximal means away from the heart while distal means toward the heart. In both the arterial and venous systems a distal point in a blood flowpath is downstream from a proximal point. The terms antegrade and retrograde flow are also used. In the arterial system, antegrade refers to flow away from the heart while retrograde refers to flow toward the heart. In the venous system, these terms are again reversed. Antegrade means toward the heart while retrograde means away from the heart.

SUMMARY OF THE INVENTION

The present invention relates to devices and methods for providing a valve within a fluid-bearing vessel within the body of a human. The present invention further relates to intravascular filters capable of filtering particulate debris flowing within a vessel. The present invention further relates to devices and methods for performing the repair or replacement of cardiac valves.

One aspect of the present invention involves methods and devices of performing aortic valve repair or replacement. In one form, the method involves the steps of inserting at least a temporary valve and a temporary filter into a segment of the aorta. Following placement of these devices, various procedures can be carried out on the aortic valve. Following the procedure, the temporary valve and temporarily filter can be removed.

The temporary valve acts to restrict retrograde blood flow while allowing antegrade flow. Generally, the valve allows forward or antegrade flow during the systolic phase of cardiac rhythm while obstructing flow during the diastolic phase. The valve serves to assist or replace the function of the native aortic valve while a procedure is performed on the native valve. The temporary valve means can be one of a variety of possible designs. The embodiments described below are merely illustrative examples and do not serve to limit the scope of this invention.

The temporary valve can be placed in any suitable location within the aorta and can be inserted either directly into the aorta itself or advanced into the aorta from a peripheral vessel such as the femoral or axillary artery. The temporary valve is preferably inserted into the vascular system in a compressed state requiring a relatively small insertion hole and expands or is expanded within the aorta at a desired site. It can then be compressed for removal. In its expanded state, the valve can occupy the entirety of the aorta's flow path, although this is not a requirement of the present invention and may not be preferred in certain patients with extensive atherosclerotic disease in the aorta. The temporary valve, therefore, can, but does not need to contact the wall of the aorta and can act to obstruct all or only a portion of the aorta's flow path.

The temporary filter acts to prevent emboli that may be dislodged during the valve procedure from moving distal to the filter. In a preferred method of use, the filter is placed in the aorta proximal to the braciolcephalic artery to prevent emboli from reaching the brain. The filter can be one of a variety of designs, including, but not limited to a mesh filter with a pore size smaller than the dimensions of anticipated embolic particles. The filter can be inserted directly into the aorta or advanced into the aorta from a peripheral artery. It is preferably inserted in a compressed state and expands or is expanded to a larger state at a desired site within the aorta.

The temporary filter and temporary valve can be separate elements or part of a single device. They may be affixed to various tubes, rods, wires, catheters, etc., to aid in their insertion into and removal from the vascular system.

Once the temporary valve and filter have been placed within the aorta, various procedures can be performed safely on the aortic valve while the heart is beating. This includes, but is not limited to, balloon aortic valvuloplasty, or removal of the aortic valve, followed by placement of a permanent valve prosthesis. The temporary valve, temporary filter, or both may be designed with lumens through which various procedure instruments can be placed. Instruments might also be passed around these devices or through a site in the aorta proximal to them.

Another aspect of the present invention is a method of performing a procedure on a beating heart involving, at a minimum, inserting into the aorta, a temporary valve, as described above, removing at least some portion of the native aortic valve, and placing a permanent valve prosthesis at a site within the aorta. The temporary valve allows removal of the native valve while reducing the risk of heart failure due to insufficiency of the native valve. Removal of at least some portion of the native valve can be carried out with one or a variety of tools that can be inserted either directly into the aorta or through a peripheral artery and advanced to the native valve. Similarly, the permanent valve prosthesis can be inserted either directly into the aorta or advanced into the aorta from a peripheral artery. The valve prosthesis is preferably inserted in a compressed state and expands or is expanded at the desired implantation site. The implantation site is preferably proximal to the coronary arteries, but can be at any suitable location in the aorta. The valve can be one of a variety of types known in the art, but is preferably a flexible valve suitable for inserting into an artery in a compressed state. This method can further involve the placement of a temporary filter as described above to reduce the risk of emboli generated during manipulation of the native valve. As described above, the temporary filter can be a separate device or an integral component of the temporary valve.

Any procedure performed using the disclosed methods can be assisted by one of a variety of visualization technologies, including, but not limited to, fluoroscopy, angioscopy and/or epi-cardial, epi-aortic, and/or trans-esophageal echocardiography. These methodologies allow real-time visualization of intra-aortic and intra-cardiac structures and instruments.

Specific reference is made to procedures performed on the aortic valve in this description, however the methods and devices described herein could be applied to other valves within the heart. The devices described above and in the claims below can be used as part of procedures performed on cardiac valves, but their use is not restricted to this limited application.

DESCRIPTION OF THE DRAWING

For a fuller understanding of the nature and objects of the present invention, reference should be made to the following detailed description taken in connection with the accompanying drawings, in which:

FIGS. 2A-2C depict another embodiment of a temporary, filter device. A small balloon located about the exterior of the cannula of this device forces blood to flow through a filter when inflated;

In FIG. 12, components of the valve pieces are shown in cross section except for backing element 110 and valve 111;

FIGS. 13A, 13B, 13C, 13C', 13D and 13D' depict a series of cross-sectional views of the valve assembly illustrated in FIG. 12;

FIG. 13A depicts the valve of the exemplary valve assembly of FIG. 12 in a compressed state within a delivery cannula 105;

FIG. 13B depicts the valve of FIG. 13A advanced outside of delivery cannula 105;

FIG. 13C depicts the expanded valve of FIG. 13A seen looking down the long axis of the vessel into which it is deployed. The valve is expanded by pulling back on button 101. In FIG. 13C, the valve is open, allowing flow through flexible loop 109. This depiction represents the state of the valve during the systolic phase when placed in the aorta and acting to support the aortic valve;

FIG. 13C' is the same as FIG. 13C with the valve assembly viewed along a radius/diameter of the vessel into which it is deployed. Valve leaflets 111 extend away to the right (as shown) of flexible loop 109;

FIG. 13D depicts the expanded valve of FIG. 13A seen looking down the long axis of the vessel into which it is deployed. In FIG. 13D, the valve is in a closed position, preventing flow through flexible loop 109. This depiction represents the state of the valve during the diastolic phase when placed in the aorta and acting to support the aortic valve.

FIG. 13D' is the same as FIG. 13D with the valve assembly viewed along a radius/diameter of the vessel into which it is deployed. Valve leaflets 111 are collapsed against backing 110;

FIG. 14A is a lateral view, showing partial deployment into the vessel. FIG. 14B is a lateral view of the deployment of FIG. 14A, showing a rod 106 positioning the temporary valve into the vessel. In this view, the temporary valve is beginning to unfold and expand. FIGS. 14C and 14D show similar views with the temporary valve somewhat more deployed;

FIGS. 23A and 23B depict a method for repairing a stenotic aortic valve, in accordance with the invention;

DESCRIPTION OF THE PREFERRED EMBODIMENTS

The methods and devices of the present invention can be used for performing procedures on cardiac valves without cardiac arrest or cardiopulmonary bypass. Various embodiments of the methods and devices are described to clarify the breadth of the present invention.

Preferred Embodiments—Temporary Filter Device

One critical aspect of any intravascular procedure that potentially involves the liberation of embolic material is the prevention of stroke and other ischemic events. Below, numerous temporary filter devices are described that allow the passage of procedure instruments into the vascular system while filtering blood passing through the lumen of the vessel into which the instrument is placed.

FIGS. 1A-1F depict multiple stages of deployment of an exemplary temporary filter device 10 of the present invention. This device is particularly useful during the manipulation and/or resection of a cardiac valve.

Figure 1A:
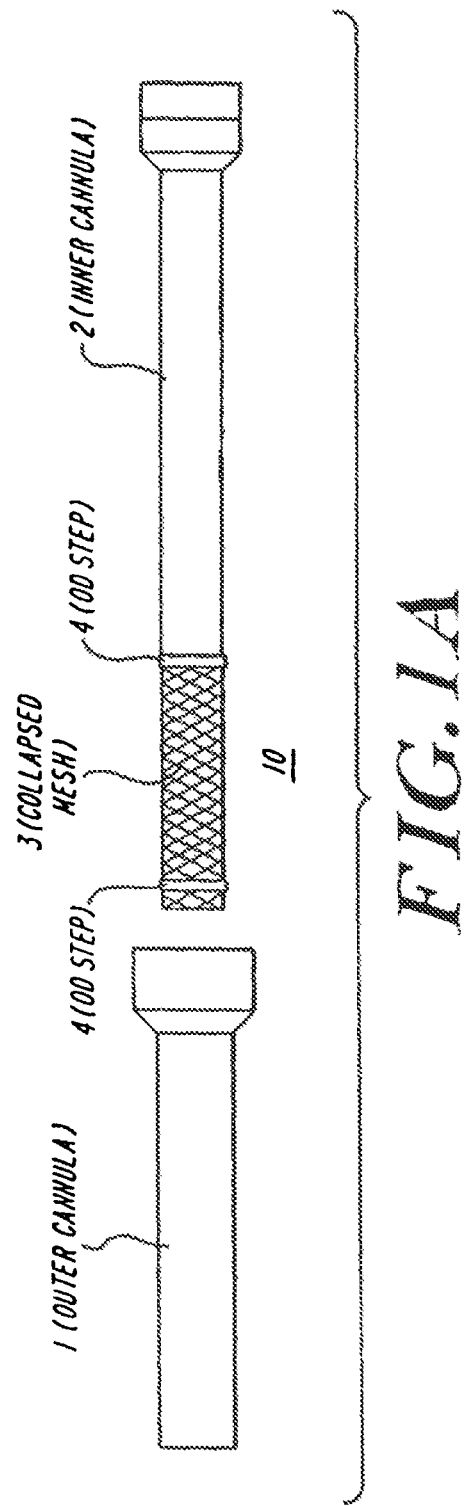
FIGS. 1A-1F depict various phases in the deployment of an exemplary filter device of the present invention.

FIG. 1A shows the three primary components of the filter device 10—outer cannula 1, inner cannula 2, and expandable mesh 3. Outer cannula 1 has an inner diameter that is greater than the outer diameter of inner cannula 2. Mesh 3 is generally tubular when collapsed and at least conical in part when expanded, and is located on the outside of inner cannula 2. The apex of the conical portion of mesh 3 is movably attached to inner cannula 2 along a length proximal (to the right) of inner cannula 2's distal tip. Collapsed mesh 3 is restrained on inner cannula 2 between two OD steps 4 rigidly affixed or integral to inner cannula 2. These OD steps may be greater than the generalized outer diameter of inner cannula 2 or may mark the ends of a reduced diameter section of inner cannula 2. The apex of mesh 3 is free to slide along and rotate about inner cannula 2's length between the two OD steps. Expandable mesh 3 may be affixed to a ring (not shown) with an inner diameter larger than the outer diameter of cannula 2 along this length. This allows the cannula to be moved along and rotated about its long axis within a tubular vessel without the expandable means and filter material moving against and abrading the vessel wall. This feature may act to minimize the risk of dislodging embolic material from the vessel wall during manipulations required by the procedure.

Figure 1B:
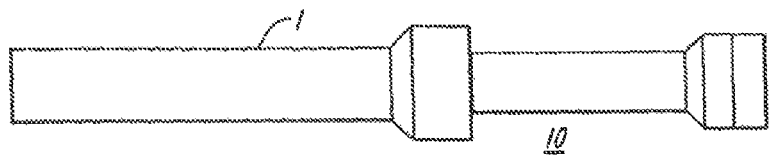
Figure 1C:
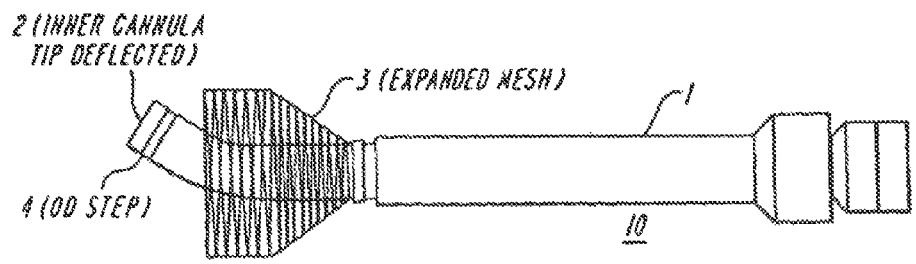
Figure 1D:
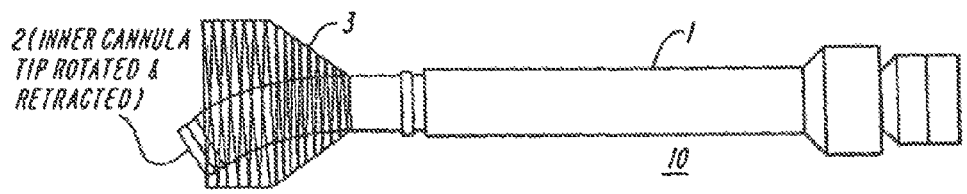
Figure 1E:
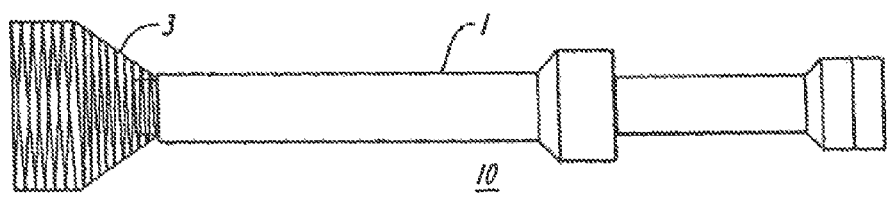

To maintain its collapsed state in the embodiment of FIGS. 1A-1F, the self-expanding, mesh 3 is positioned against the outer surface of inner cannula 1. As shown in FIG. 1E (but not shown in FIGS. 1A-1F), a filter material 71, such as woven nylon mesh with a defined pore size, may be positioned over the mesh 3. Such a material is optional and may be used to cover at least some portion of expanded mesh 3 and may be placed on either the outer or inner surface of mesh 3.

The outer and inner cannulae can be constructed from any one of a variety of materials, including, but not limited to, various plastics, rubber, and metals. They can be either wholly rigid or flexible in nature. They can be rigid along most of their lengths with a small flexible region or regions that allow the cannulae to bend. There can further be a valve means (not shown) situated along the interior of inner cannula 2 that prevents the flow of blood while allowing passage of instruments through inner cannula 2. Either or both of inner cannula 2 and outer cannula 1 can have additional degassing ports (not shown) exterior to the vascular system to allow removal of air and other gases from the interiors of the cannulae.

Expandable mesh 3 can also be made from any one of a variety of materials, but is preferably constructed from elastic metal woven into a tube. This tube preferably has a first diameter in an expanded state and a second, smaller diameter in a compressed state. The first diameter is preferably similar to that of the aorta or vessel in which the filter is used. The mesh itself can act as a filter or filter material can be attached along its interior or exterior. This embodiment is merely an illustrative example. There are many other potential embodiments of a filter means that could be imagined without departing from the spirit of the present invention.

FIG. 1B depicts assembled filter device 10, with the distal end of the inner cannula 2 inserted into the proximal end of the outer cannula 1.

FIG. 1C depicts assembled filter device 10 with the outer cannula 1 retracted proximally, exposing mesh 3 and allowing its free to expand against the inner wall of the vessel into which it is deployed. In this embodiment, mesh 3 expands into a conical shape, with the base of the cone extending toward the distal end of the cannulae. Inner cannula 2 has a deflected tip that bends the lumen of the cannula away from the long axis of the device. This bend assists in guiding any procedural instrument passed through the lumen of inner cannula 2 toward the wall of the vessel and/or the attachments of a cardiac valve to that wall. The mobility of mesh 3 in this figure permits this bend without altering the orientation of mesh 3 relative to the vessel into which it is inserted. As shown, the tip of inner cannula 2 extends beyond mesh 3. Moreover, in some embodiments, that tip is steerable under the remote control of a surgeon. In that configuration, a device, such as valve resecting device which extends out of cannula 2, may be steered to resect desired portion of a stenotic valve, for example. The invention may also include a fiber optic viewing assembly extending through cannula 2.

FIG. 1D depicts the device of FIG. 1C with inner cannula 2 rotated 180° about its long axis and retracted proximally. The sliding attachment of expanded mesh 3 to inner cannula 2 allows this to occur without any motion of mesh 3 relative to the vessel wall.

FIG. 1E depicts the device of FIG. 1D during removal. Outer cannula 1 is advanced over inner cannula 2 and is about to compress expanded mesh 3 and any entrapped material. The mobility of expanded mesh 3 relative to inner cannula 2 causes mesh 3 to move beyond the distal end of inner cannula 2. This ensures that embolic material captured by mesh 3 will not be trapped between mesh 3 and the exterior of inner cannula 2. This would prevent passage of outer cannula 1 over mesh 3 and inner cannula 2. With the mobility of mesh 3 relative to inner cannula 2, a much greater amount of embolic material may be trapped compared to a fixed proximal filter as described in the prior art.

Figure 1F:
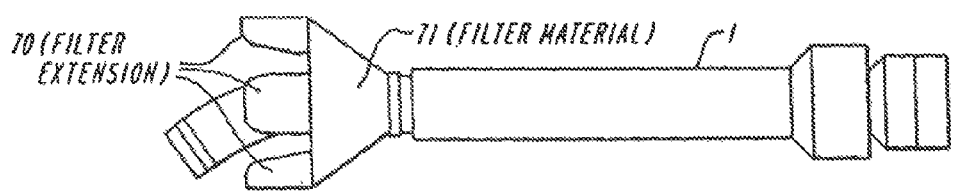

FIG. 1F depicts the device of FIG. 1D with filter material 71 added to the exterior surface of expanded mesh 3. In this embodiment, expanded mesh 3 has been shortened to just the cone portion of the prior meshes. Extending distally beyond this cone are filter extensions 70 that occupy only a portion of the circumference of a cylinder having a diameter equal to the maximum diameter of the cone-shaped mesh 3. The extensions are adapted to lie along the vessel wall and rest over the ostium of one or more arteries that branch from the vessel. The extension configuration of FIG. 1E is advantageous for filtering the ostia of branch vessels that may be located between valve commissures, such as the coronary ostia in the aorta.

For aortic valve applications, extensions 70 are preferably from three points spaced around the circumference of the cone's expanded end. These points are preferably 120 degrees apart. Each extension 70 is preferably a hemi-circular leaflet with the diameter of the hemi-circle being located about the circumference of the cone's base. When deployed, device 10 is oriented so that the base of the cone is expanded toward the aortic valve. The shape of the three leaflets allows the filter to be expanded or advanced along the wall of the aorta beyond the plane created by the three apices of the aortic valve commissures. In this position, the leaflets cover and filter the left and right coronary ostia while the filter cone filters blood flowing through the aorta.

In the expanded position, the three extensions 70 can be biased against the wall of the aorta by expandable mesh 3, by the stiffness of the filter material 71, or by the shape of the filter itself. Extensions 70 can further be designed to exploit pressure within the vessel to compress them against the vessel wall.

Such an expandable filter acts to filter just the branch vessels with the conical portion of the expanded mesh left uncovered by filter material 71. In such an embodiment, either the partial filter extensions can be employed (as in FIG. 1F) or full cylindrical filters (not shown) that cover the entire circumference of the vessel wall can be employed.

FIGS. 2A, 2B, and 2C show an alternate embodiment of a filter that can be used to filter emboli from blood flowing through a vessel. Filter 20 consists of cannula 17, a valve located within the interior of the cannula (not shown), an expandable means depicted as balloon 19, and a filter depicted as mesh 18. The valve interior to cannula 17 acts to prevent the flow of blood out of the vessel through cannula 17 while allowing the passage of instruments through the lumen of cannula 17. This valve is positioned to the right of filter 18 as viewed in FIGS. 2A and 2B. Balloon 19 can be expanded by the injection of gas or liquid through port 21. Once inflated, balloon 19 obstructs the flow path of the vessel exterior to cannula 17. Hence, the blood must flow into the interior of cannula 17 and exit the cannula through filter 18. In this way, emboli are prevented from flowing past the filter. In FIG. 2B, an intravascular instrument 5 has been passed through the inner lumen of cannula 17. As instrument 5 does not occupy the entire interior flow area of cannula 17, blood can flow around instrument 5, into cannula 17 and through filter 18. FIG. 2C is an end-on view of filter 20 and instrument 5 from the left side as viewed in FIG. 2B. In this figure, the blood flow path is annulus 22 formed by the inner wall of the cannula 17 and the shaft of the instrument 5. Additional blood flow paths could be provided through portions of balloon 19. Optionally, these paths additionally have a filter mesh covering the path. Filter 20 can be used in a variety of intravascular procedures that would benefit from the filtration of blood.

Preferred Embodiment—Combined Temporary Valve Devices

In order to carry out procedures on cardiac valves without cardiopulmonary bypass, it is critical to support the function of the valve during the procedure. Numerous preferred embodiments of temporary valves that perform this function are disclosed below. Many of these valves are combined with filters to further limit the risk of ischemic events that might result from liberated embolic material.

FIGS. 3-7 depict one embodiment of such a combined valve and filter device. As depicted in FIGS. 3A and 3B, endovascular procedure catheter 2' is inserted into the host. It is positioned over a guide wire 800 at its desired location, for this example in the ascending aorta above the coronary arteries and below the brachiocephalic artery. Guide wire 800 and guiding catheter 700 can then be removed.

Once endovascular procedure catheter 2' is in position, temporary one way valve 26, the selectively permeable, filtering membrane 3', and mounting ring 900 are deployed. Deployment comprises the controlled, adjustable increase in the diameter of valve 26, membrane 3', and/or mounting ring 900 until they abut or nearly abut the inner wall of the vessel.

Temporary one-way valve mechanism 26 can be comprised of any type of one way valve. The critical function of valve 26 is to limit the aortic insufficiency and thus, the amount of volume overload on the heart generated by resecting or manipulating the diseased or damaged host valve. This will allow procedures to be performed on the valve and replacement of the valve without the need for partial or complete cardiac bypass or cardiopulmonary bypass.

Next, the host aortic valve is resected, removed or manipulated. If the valve is to be replaced, the new cardiac valve is implanted. This valve can be mounted on endovascular procedure catheter 2' or can be delivered through another port of entry or cannula. Upon completion of the procedure, all devices are retracted and removed.

The illustrated exemplary endovascular procedure catheter 2' is a cylindrical sleeve that is made of a flexible material. It is durable and resistant to thrombogenesis.

It has several associated components:
- a lumen for the passage of devices e.g. imaging devices, tissue resecting devices, valve deployment devices, the new valve, or any other device necessary to perform endovascular procedures on the endovascular vessels or valves
- a guiding catheter 700 which is tapered on the end and extends out of the working port of the endovascular procedure catheter 2'; catheter 700 helps in positioning the endovascular procedure catheter
- a one way valve 25 inside the catheter which limits blood loss during the procedure
- temporary one way valve 26
- a selectively permeable, filtering membrane 3'
- an endovascular mounting ring 900 onto which temporary valve 26 and/or selectively permeable, filtering membrane 3' are mounted
- a stent system 950-958 which deploys the mounting ring 900, temporary endovascular one-way valve 26, and selectively permeable filtering membrane 3' by interacting with guiding catheter 700 and endovascular procedure catheter 2'
- several holes 600 in the wall of the distal end of the catheter which may augment antegrade flow of blood during the procedure.

The aforementioned components may be used alone or in combination during endovascular procedures.

The lumen of endovascular procedure catheter 2' functions as a working port allowing for the passage of devices such as imaging devices, tissue resecting devices, or any other device necessary to perform endovascular procedures on the endovascular vessels or valves.

Endovascular procedure catheter 2' itself has a one-way valve 25 in its lumen (indicated in phantom) to minimize the loss of fluid i.e. blood during the procedure. This one-way valve can be of any configuration as long as it serves to permit the passage and removal of instruments through the lumen of the endovascular procedure catheter and inhibits retrograde blood flow through the endovascular procedure catheter. It is located proximal to side holes 600 of endovascular procedure catheter 2'.

Temporary valve 26 is made of a flexible, durable, non-thrombogenic material. Valve 26 can be any type of one-way valve and consist of as many or few leaflets as desired as long as it permits the antegrade flow of blood and prevents the retrograde flow of blood. This minimizes the development of aortic insufficiency created during manipulation of the valve and minimizes the need for cardiac or cardiopulmonary bypass. Valve 26 depicted in FIG. 3A, 3B and FIG. 4A, 4B is a bileaflet valve mounted on mounting ring 900. It permits antegrade blood flow through filter 3' in the open position and inhibits retrograde blood flow by collapsing against filter 3' in the closed position. The valve mechanism is a simple one way, single orifice valve which is mounted on the stabilizer. However, the valve can sit independent of mounting ring 900 and as aforementioned can take on any shape as long as it functions as a one way valve.

The center of selectively permeable filtering membrane 3' is mounted on the outside wall of endovascular procedure catheter 2'. The relatively large diameter peripheral edge is mounted on mounting ring 900. It is conical in shape when deployed and sits just upstream of temporary valve 26. Filter membrane 3' is made of a flexible, durable, non-thrombogenic material that has pores that are sized to permit select fluids through (i.e. blood and blood components) but prevents the flow or embolization of debris generated during the endovascular procedure. By placing it upstream of temporary valve 26 it prevents prolapse of the temporary valve leaflets.

Figures 3A, 3B:
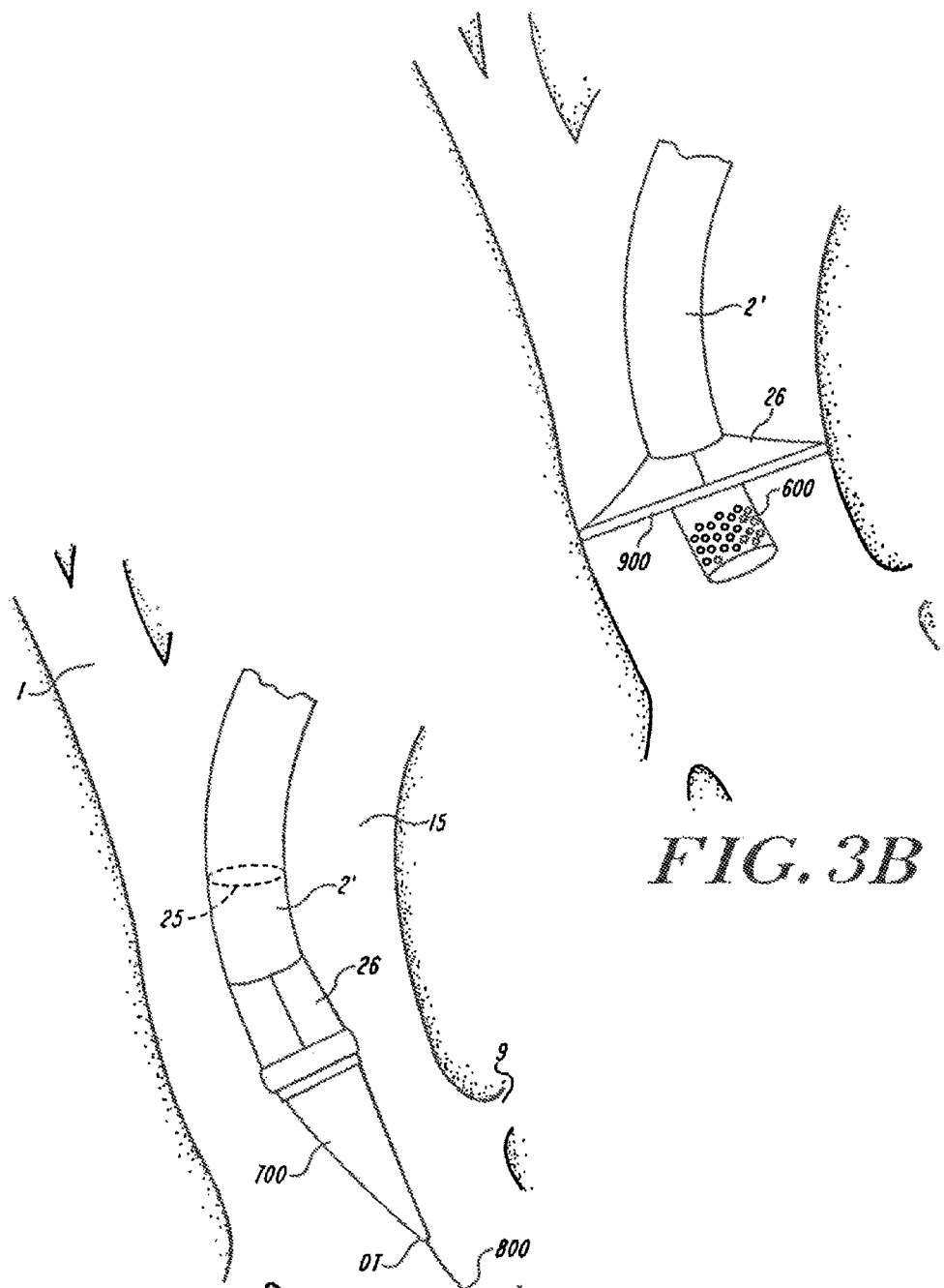
FIG. 3A shows a schematic representation of an endovascular procedure catheter of the invention, with the one-way valve and filter membrane in a retracted position.
FIG. 3B depicts the endovascular procedure catheter of FIG. 3A following deployment of the one-way valve and filter membrane.
Figure 4A:
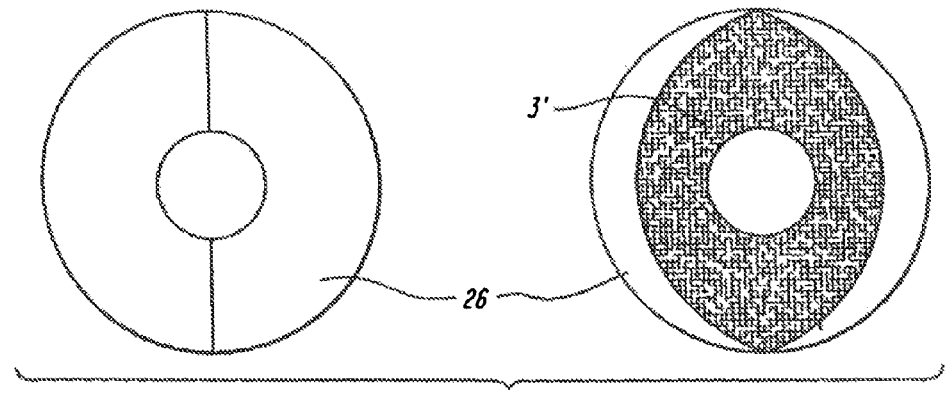
FIG. 4A depicts valve and filter components of the procedure catheter of FIG. 3A viewed along the retrograde flow path. The valve is closed on the left portion of FIG. 4A, preventing retrograde flow, and open on the right portion of FIG. 4A, allowing antegrade flow.
Figure 4B:
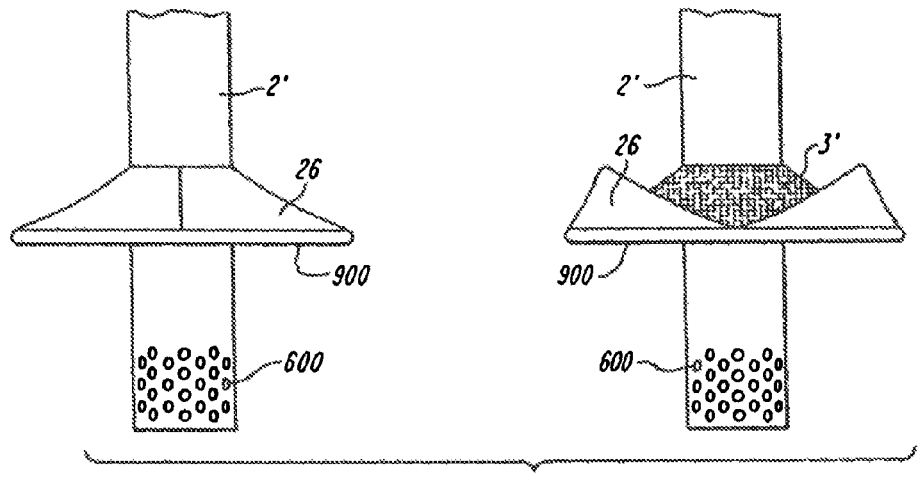
FIG. 4B depicts the "valve open" (left portion) and "valve closed" (right portion) positions of the procedure catheter of FIG. 3A viewed along an axis perpendicular to the flow path.
Figure 5A:
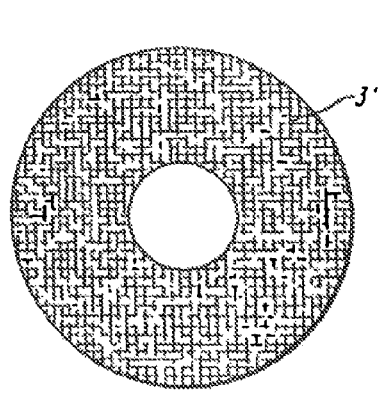
FIG. 5A depicts the filter membrane element of the procedure catheter of FIG. 1A as viewed along the flow path within a vessel.
Figure 5B:
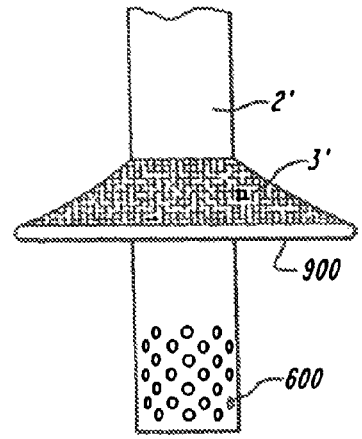
FIG. 5B depicts the procedure catheter of FIG. 3A with the one-way valve removed.

In order to assist in positioning and removal of endovascular procedure catheter 2', a tapered guiding catheter 700 of the size of the internal diameter of endovascular procedure catheter 2' is placed inside endovascular procedure catheter 2' as depicted in FIG. 3A. In a preferred form, the tapered end at the distal tip DT extends approximately 2 centimeters beyond the distal end of endovascular procedure catheter 2'; but other extension lengths may be used. Guiding catheter 700 is made of flexible material and the end is soft to prevent injury to the vessels during placement of endovascular procedure catheter 2'. Guiding catheter 700 has a lumen of such a size as to permit its passage over guide wire 800.

Figure 6:
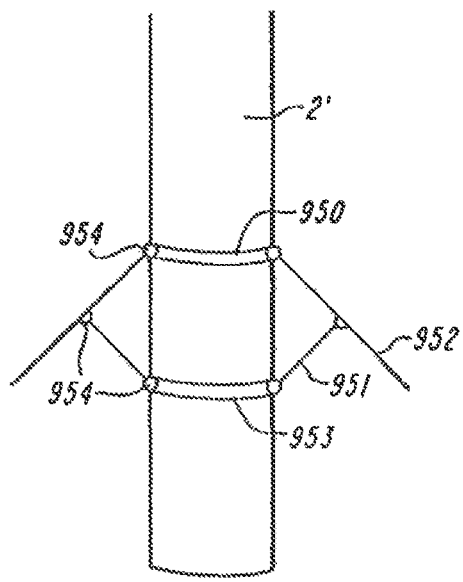
FIG. 6 depicts an exemplary deployment system for the temporary valve and filter elements of the endovascular procedure catheter of FIG. 3A.
Figure 7A:
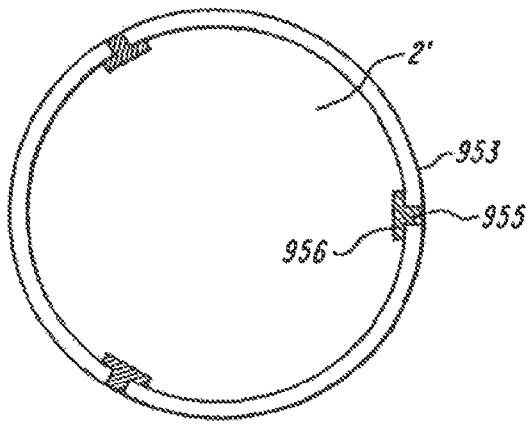
FIGS. 7A-7D depict exemplary elements used to aid in deployment of the temporary valve and filter element of the endovascular procedure catheter of FIG. 3A.
Figure 7B:
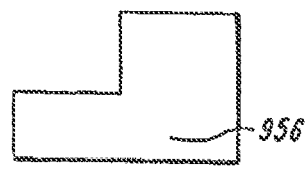
Figure 7C:
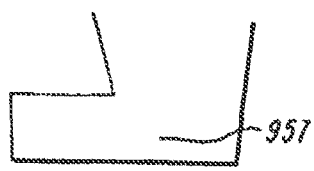
Figure 7D:
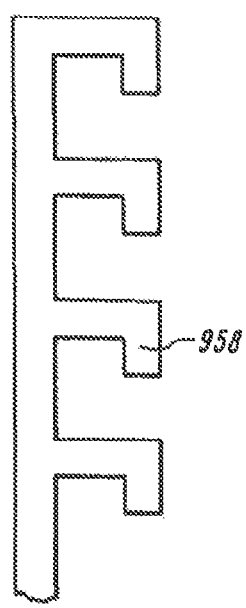

Guiding catheter 700 also serves to deploy and retract mounting ring 900, temporary valve 26, and filter membrane 3'. FIG. 6 illustrates an exemplary deployment assembly DA for membrane 3'. That assembly DA includes elements 950-958, described in detail below. As depicted in FIG. 7A, guiding catheter 700 has slots distally which engage extension arms 955 of struts 952 that support mounting ring 900.

Mounting ring 900 is mounted on the outside of endovascular procedure catheter 2' by struts 952. Mounting ring 900 is comprised of a flexible, durable, nonthrombogenic material which abuts the inner lumen of the vessel when deployed. Temporary valve 26 and/or selectively permeable membrane 3' are mounted on mounting ring 900. When mounting ring 900 is deployed so are the mounted components. Mounting ring 900 is deployed in a controlled, adjustable way. Struts 952 are connected to mobile ring 953 and fixed ring 950 which is mounted on endovascular, procedure catheter 2' as shown in FIG. 6. Mobile ring 953 has extensions 955 which extend into the lumen of endovascular procedure catheter 2' by passing through slots in the wall of endovascular procedure catheter 2'. These extensions are engaged by grooves 957 in the wall of guiding catheter 700. Thus as guiding catheter 700 is withdrawn or advanced inside endovascular procedure catheter 2', mounting ring 900 is deployed or retracted in an umbrella-like manner. Once mounting ring 900 is deployed to the desired diameter, it is "locked" into place by engaging extension arms 955 into locking slots 958 cut into the wall of endovascular procedure catheter 2'. At this point, guiding catheter 700 is disengaged from extension arms 955 and removed while mounting ring 900 remains deployed.

As shown in FIG. 6, the strut mechanism consists of struts 952, rings 950 and 953, and hinges 954. The strut mechanism depicted here consists of three struts 952 that connect mounting ring 900 to the fixed proximal ring 950 that is mounted on the outside of procedure catheter 2'. These struts are also connected to support arms 951 which extend to mobile distal ring 953 also mounted to the outside of endovascular procedure catheter 2'. Distal ring 953 has extension arms 955 which extend through the slots in the wall of procedure catheter 2' as shown in FIG. 7. Mounting ring 900 is expanded by moving support rings 953 and 950 relative to each other. Struts 952 and arms 951 are hinged at pivot points 954.

Figure 8A:
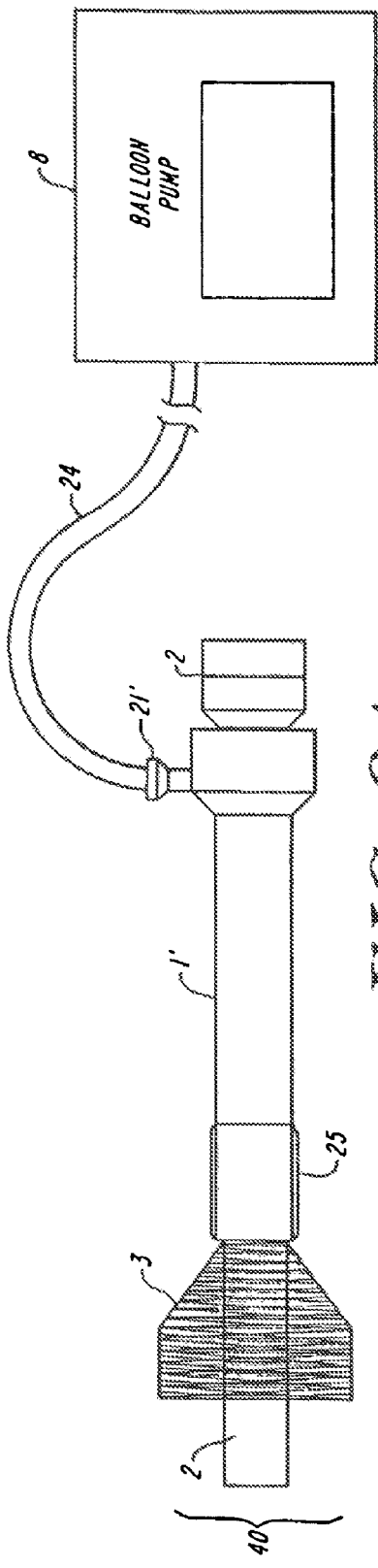
FIGS. 8A and 8B depict another embodiment of a temporary valve and filter device of the invention. The temporary valve of the depicted device is a small balloon on the outside of an inner cannula. The balloon is inflated to prevent retrograde flow and deflated to allow antegrade flow.
Figure 8B:
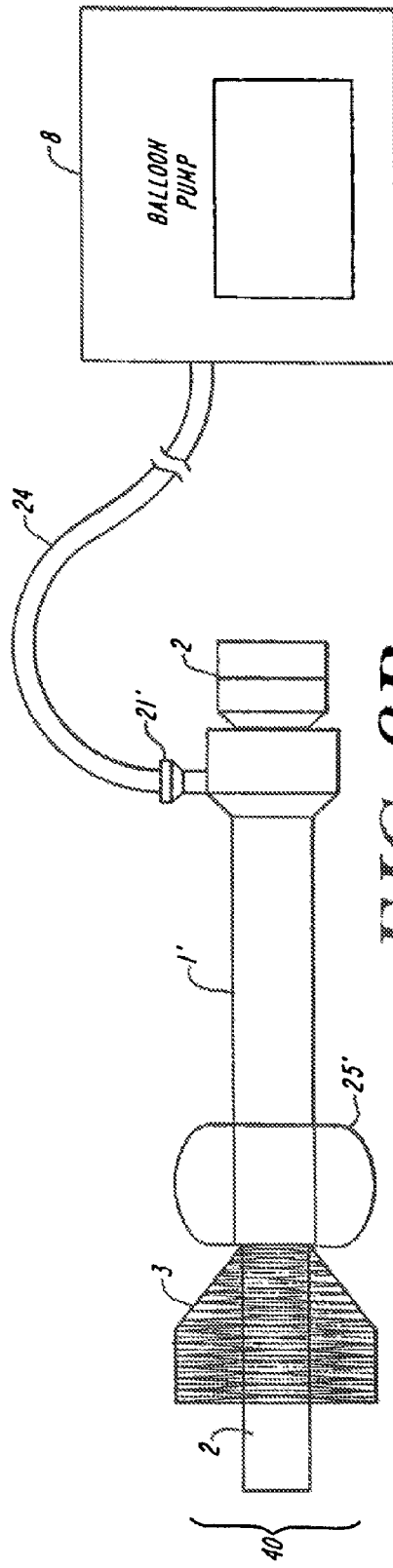

FIGS. 8A and 8B illustrate another embodiment of a combined valve and filter device for use in intravascular procedures. The filter means of device 40 is the same as device 10 depicted in FIGS. 1A-1E. A temporary valve, depicted in FIGS. 8A and 8B as expandable balloon 25, is situated on the exterior of outer cannula 1' of the device. A continuous lumen (not shown) extends from the interior of balloon 25 to port 21'. Port 21' is connected to balloon pump 8 by tube 24. FIG. 8A depicts a device 40 with filter 3 deployed and balloon 25 deflated during the systolic phase of the cardiac rhythm. FIG. 8B shows balloon 25 in an inflated state 25' during the diastolic phase. Similar to device 10 of FIG. 3, inner cannula 2 may have a lumen through which instruments can be passed to effect an intravascular procedure. In these figures, the filter is shown to the left of the valve. In other embodiments, this relationship may be reversed.

Figure 9A:
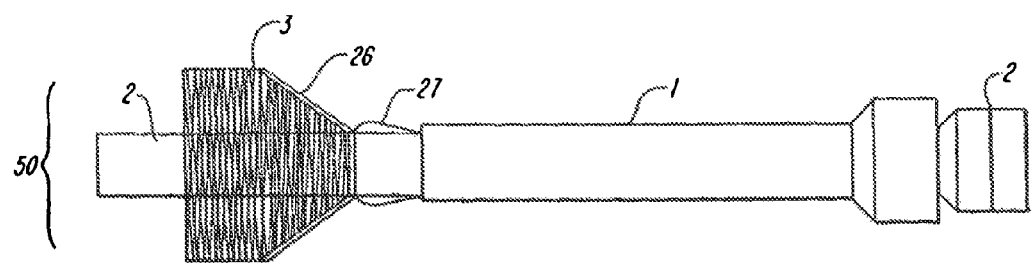
FIGS. 9A and 9B depict another embodiment of a temporary valve and filter device in accordance with the invention. Flaps of material collapse against the expandable mesh of the temporary filter to prevent retrograde flow.
Figure 9B:
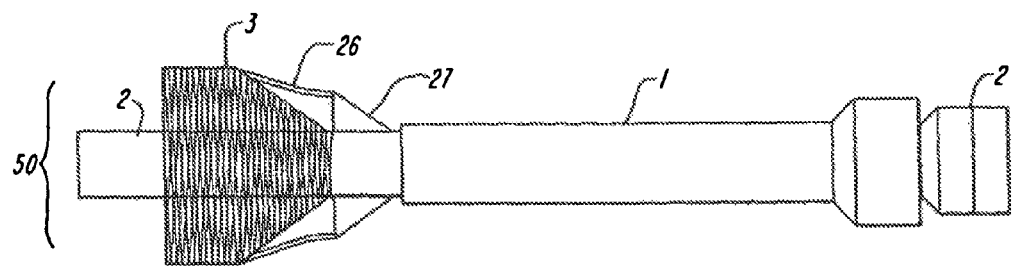

FIGS. 9A and 9B show yet another embodiment of a combined valve and filter device for use in intravascular procedures. Device 50 is the same as device 10 in FIGS. 1A-1E with the addition of valve means 26 that covers the surface of expanded filter 3. In this embodiment, valve means 26 consists of one or a number of thin sheets of material that are attached to the exterior of the base of the cone formed by the expanded mesh filter 3. The sheet material is relatively free to move at the apex of the cone such that mesh filter 3 and the sheet material act in concert as a flap valve. As shown in FIG. 9B, blood flows through filter 3 from the interior of the cone causing flap valve 26 to open and allow flow. As shown in FIG. 9A, blood moving toward the exterior of the cone causes the sheet material of flap valve 26 to move against the exterior of the cone, preventing flow through filter 3. The device can be delivered with mesh filter 3 and flap valve 26 in a compressed state within outer cannula 1 similar to FIG. 3B. Mesh filter 3 and valve 26 then expand once outer cannula 1 is retracted. The sheet material can additionally be affixed to a more proximal segment of inner cannula 2 by thin filaments 27 or the like to aid in returning valve 26 and filter 3 to a collapsed state by advancing the outer cannula 1.

Figure 10A:
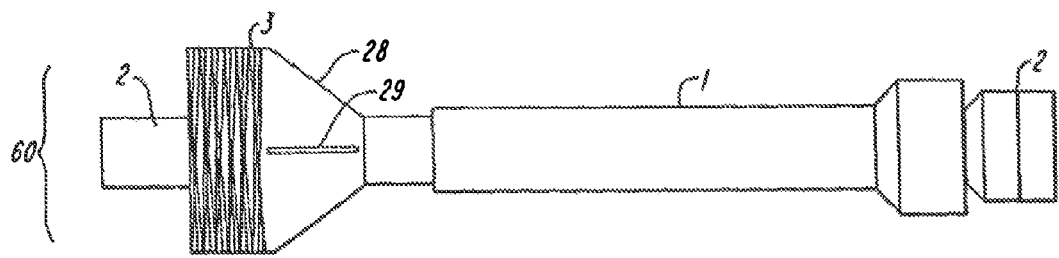
FIGS. 10A and 10B depict another embodiment of a temporary valve and filter device in accordance with the invention. Slits cut in a valve material located about the expandable mesh provide a path for blood during antegrade flow and close against the expandable mesh during retrograde flow.
Figure 10B:
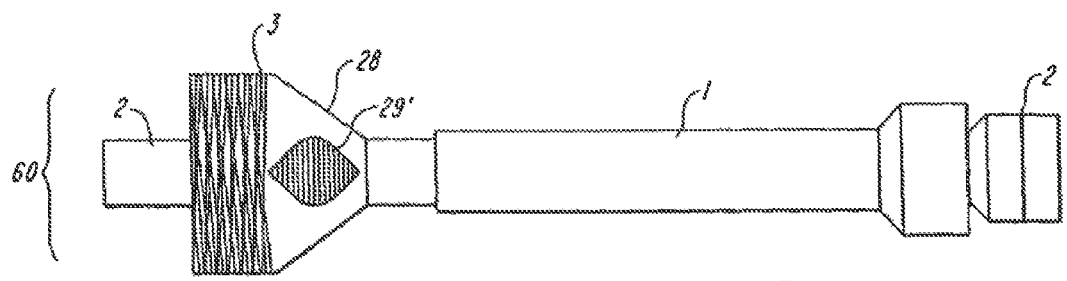

FIGS. 10A and 10B show another embodiment of a combined valve and filter device. Device 60 is the same as device 10 in FIGS. 1A-1E with the addition of valve 28 that covers the surface of expanded filter 3. Valve 28 consists of a singular sheet of material that covers the entirety of the outer surface of the cone portion of expanded mesh filter 3. It is attached, at a minimum, to the cone's base and either its apex or the exterior of inner cannula 2 near the apex. Slit 29 is cut through the sheet between these attachment sites. As shown in FIG. 10A, slot 29 closes against filter 3' during retrograde flow, i.e. flow from the cone's apex toward its base, preventing the passage of blood through expanded filter 3. As shown in FIG. 10B, slit 29 moves to an open state 29' during antegrade flow, i.e. from the cone's base toward its apex, allowing passage of blood through expanded filter 3. Slit 29 is shown in these figures as being in a plane that passes through the long axis of inner cannula 2, however other orientations are possible. A singular slit is shown, although there could be multiple slits. The sheet material comprising valve 28 can be attached at additional sites along mesh filter 3 to assist in its function.

Figure 11A:
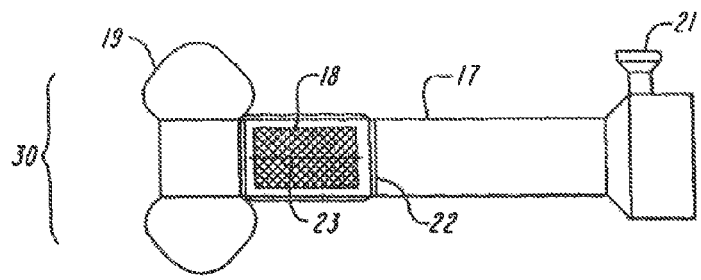
FIGS. 11A and 11B depict the device of FIGS. 2A-C with the addition of a one-way valve.
Figure 11B:
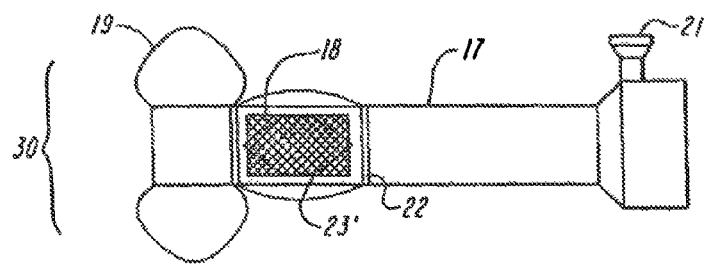

FIGS. 11A and 11B depict a combined valve and filter device 30. The filter means of device 30 is the same as filter device 20 shown in FIGS. 2A-2C. In this embodiment, valve 22 is placed around the exterior of cannula 17, covering filter 18. Valve means 22 is preferably a flexible sleeve of material such as silicone rubber. A slit 23 has been cut through the sleeve along its length. Slit 23 is normally closed, but opens under positive pressure within cannula 17. Hence, when this device is placed in the arterial system with the distal end (near balloon 19) pointed proximally, slit 23 opens during the systolic phase of cardiac rhythm, allowing blood flow through filter 18, and closes during the diastolic phase, preventing blood flow through filter 18. FIG. 11A depicts valve 22 in a closed position. FIG. 11B depicts valve means 22 in an open position. Similar to device 20, device 30 may be configured with additional flow paths (not shown) passing through balloon 19. These flow paths may have filters associated with them that act to filter blood passing therethrough. These flow paths may include additional valves that resist retrograde flow while allowing antegrade flow.

Each of the preceding filter and valve embodiments are adapted to be inserted into a vessel through an insertion site and expanded radially from the center of the vessel at a site remote from that insertion site.

Figure 12:
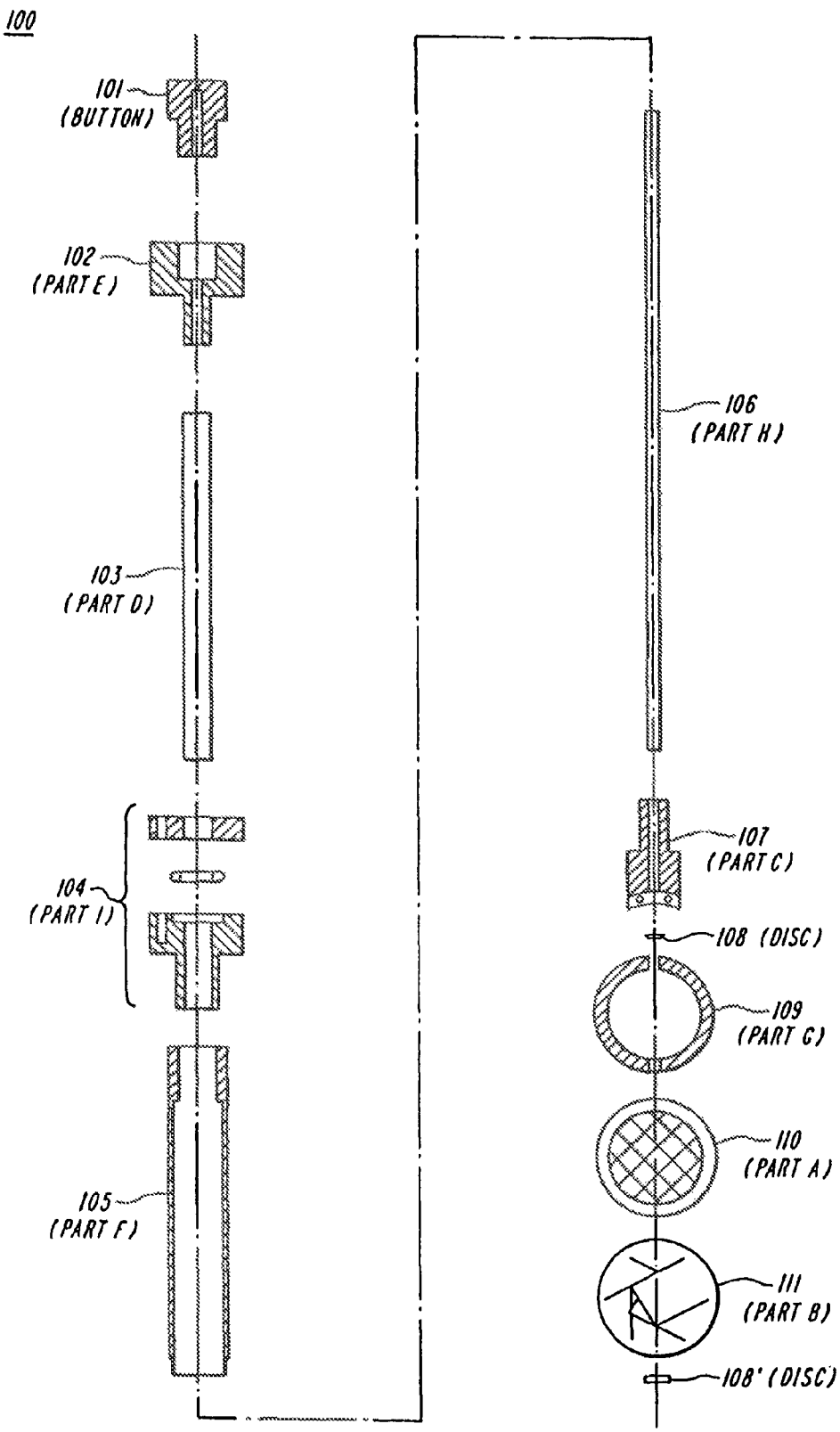
FIG. 12 depicts an exploded cross-sectional view of an alternative temporary valve assembly in accordance with the invention.
Figure 14A:
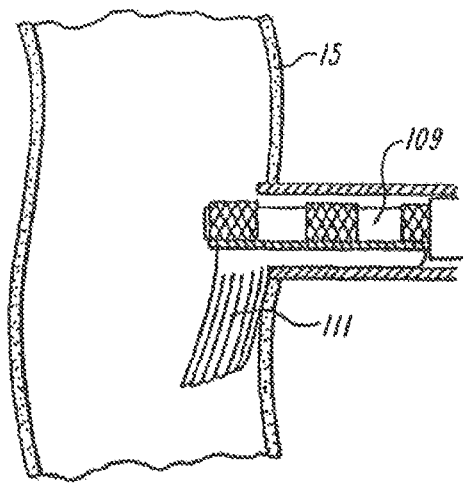
FIGS. 14A-14D depict the valve end of temporary valve assembly of FIG. 12 inserted into a vessel.
Figure 14B:
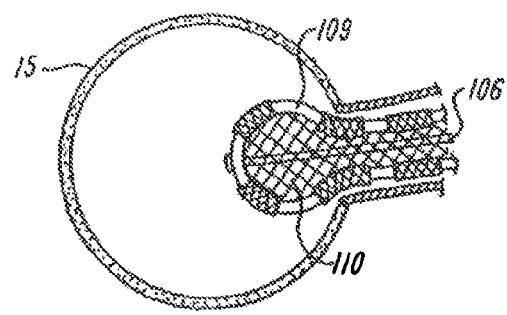
Figure 14C:
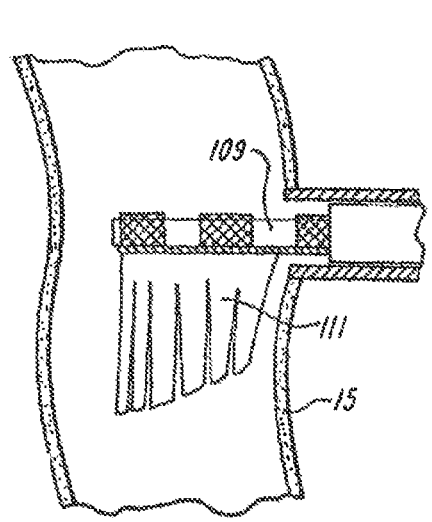
Figure 14D:
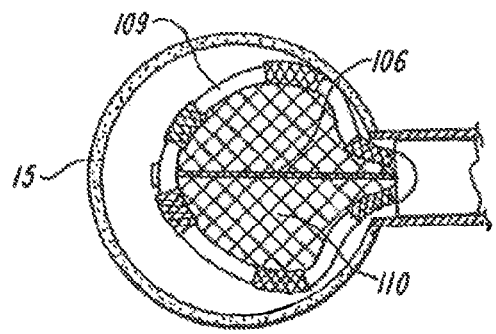

FIGS. 12-14 disclose a temporary valve assembly (with optional filter) 100 which can be inserted substantially perpendicular to the long axis of the vessel and expanded at or near the insertion site.

In a preferred form, the valve assembly 100 consists of four components—a cannula, a deformable loop, a backing element and a valve. In use, the distal end of the cannula is inserted into a vessel, the deformable loop is then advanced out of the distal end into the vessel and expanded to abut the interior wall of the vessel. The backing element spans the interior lumen of the expanded loop and is attached to the loop at least one point. The backing element is permeable to blood flow. A valve is affixed to either the expanded loop, the backing element, or both and functions to stop flow along the long axis of the vessel in a first direction through the loop by collapsing against the backing element and covering substantially all of the lumen formed by the loop. The valve further allows flow in a second, opposite direction by deflecting away from the backing element during flow through the loop in that direction.

FIG. 12 depicts the detailed construction of the valve device 100 in exploded form. Button 101 is a rigid piece with an opening that is used to attach it to a central rod 106. Rod 106 is rigid and is attachable to the valve components of the device (Parts G, A, and B, as illustrated) as well as two small discs 108 and 108'. Secondary button 102 is affixed to valve holder 107 through tube 103. Parts I form proximal seal 104 and are affixed to each other and delivery cannula 105. Tube 103 can slide through the lumens of proximal seal 104 and delivery cannula 105. Rod 106 can in turn be passed through the lumens of valve holder 107, tube 103, and secondary button 102. Proximal seal 104 includes an o-ring that seals around the exterior of tube 103. Flexible loop 109 has a hole through the center of its length seen at the base of the loop formed in the figure. A backing element 110 and valve 111 are affixed to flexible loop 109 with any suitable fixation means. Backing element 110 spans the interior of flexible loop 109. Element 110 is made of flexible material and in its preferred embodiment is a woven nylon sheet. This sheet can act to filter particulate debris from blood passing through flexible loop 109. Valve 111 is a set of valve leaflets. In this figure there are six valve leaflets. These leaflets are attached to the periphery of backing means 110, flexible loop 109 or both, for example, by way of a ring of material surrounding the leaflets. Once assembled, backing element 110, valve 111, and flexible loop 109 are affixed to valve holder 107 through the two small through-holes in valve holder 107. These through holes act as hinge points about which the ends of flexible loop 109 can pivot. Rod 106 is inserted through a central lumen in valve holder 107, superior disc 108, the hole in flexible loop 109, and finally inferior disc 108'. Discs 108 and 108' are affixed to rod 106 to immobilize the center section of flexible loop 109 relative to the lower end of rod 106. Valve holder 107 fits within the lumen of delivery cannula 105.

In a preferred embodiment of this valve assembly 100, backing element 110 is a porous sheet of material that further acts to filter blood passing through deformable loop 109. This porous sheet can be a woven material with an open area that allows the passage of blood, although other forms may be used, all within the scope of the invention.

In another preferred implementation of the device 100, deformable loop 109 is made from a strip of material with a non-circular cross section. It may have a rectangular cross-section. The thicker side of the rectangle can be positioned against the wall of the vessel. This gives the loop greater flexibility to conform easily to the shape of the wall and greater stiffness against flopping or twisting away from the vessel wall under the pressure of blood flowing through the vessel.

The valve 111 is preferably effected by a set of valve leaflets as shown. The valve leaflets can collapse, in an overlapping manner, against backing element 110 to prevent flow in a first direction through the loop 100. The leaflets may alternatively coapt against each other so as to prevent flow in the first direction. In the latter form, the device may be used without a filter (backing element), to provide a valve-only device. Generally, such a device would be used with a filter in another location.

The leaflets of valve 111 are preferably formed from thin, flexible sheets of material. There may be any number of leaflets. The leaflets may be sized to act in concert to close the flow path formed by the loop. The leaflets may alternatively be oversized, such that fewer than all of the leaflets are required to close the flow path.

In one embodiment, there may be two or more leaflets with one or some combination of the leaflets capable of closing the flow path through the loop against flow in the second direction.

The valve 111 may alternatively be a sheet of material cut with slits. The slits stay substantially closed (not parted) to prevent flow in a first direction through the flow path created by the loop 109 by collapsing against the backing element. The slits allow the passage of blood in the second, opposite direction through the flow path by parting open in the direction away from the backing element.

In a preferred method of using a valve of the form of FIGS. 12-14, the device is expanded from a point or set of points on the circumference of the vessel into which it is placed until the valve occupies substantially all of the cross sectional flow area of that vessel.

Another method of using that device of the form of FIGS. 12-14, is to insert the distal end of the device into the vessel through an entry site and expanding the valve proximate to the entry site. This allows the device to be placed easily, near the heart, during an open-chest procedure.

Another method of using the device is to insert its distal end into a vessel along a path that is substantially perpendicular to the long axis of the vessel and expand the valve about that path. In a preferred application of this method, the device is expanded until it occupies the entire flow path of the vessel and sits within a cross-section of that vessel taken perpendicular to the vessel's long axis. This minimizes the length of the vessel taken up by the temporary valve device.

Figure 15:
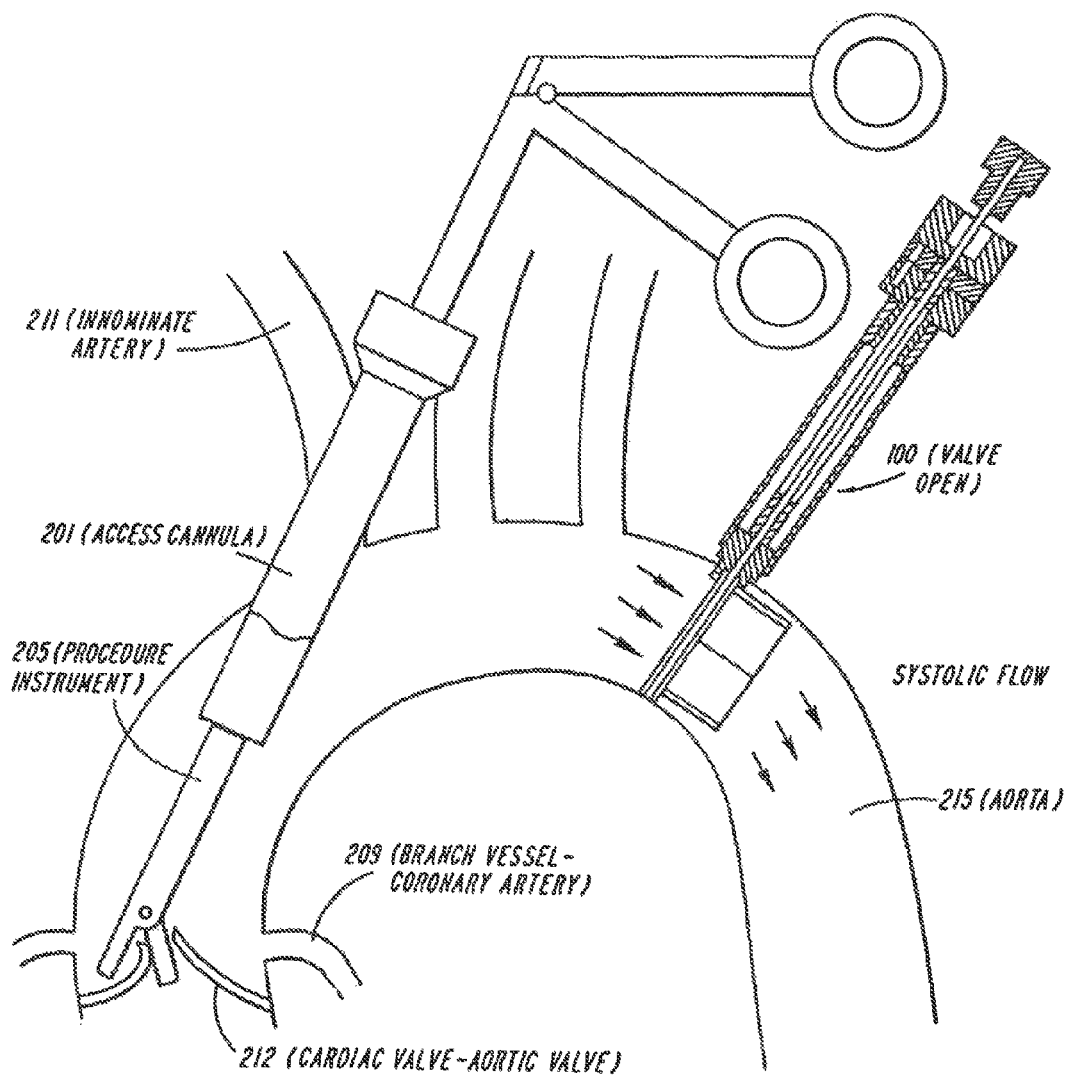
FIG. 15 depicts a temporary valve of the invention deployed in the aorta with the valve open.

FIG. 15 depicts temporary valve assembly 100, with its valve deployed in aorta 215. In this figure, a procedure is indicated as being performed on aortic valve 212 through a separate access cannula 201 using procedure instrument 205. Device 100 is shown with its valve open (as in FIG. 13C') allowing flow through flexible loop 109. This figure depicts the systolic phase of cardiac rhythm.

Figure 16:
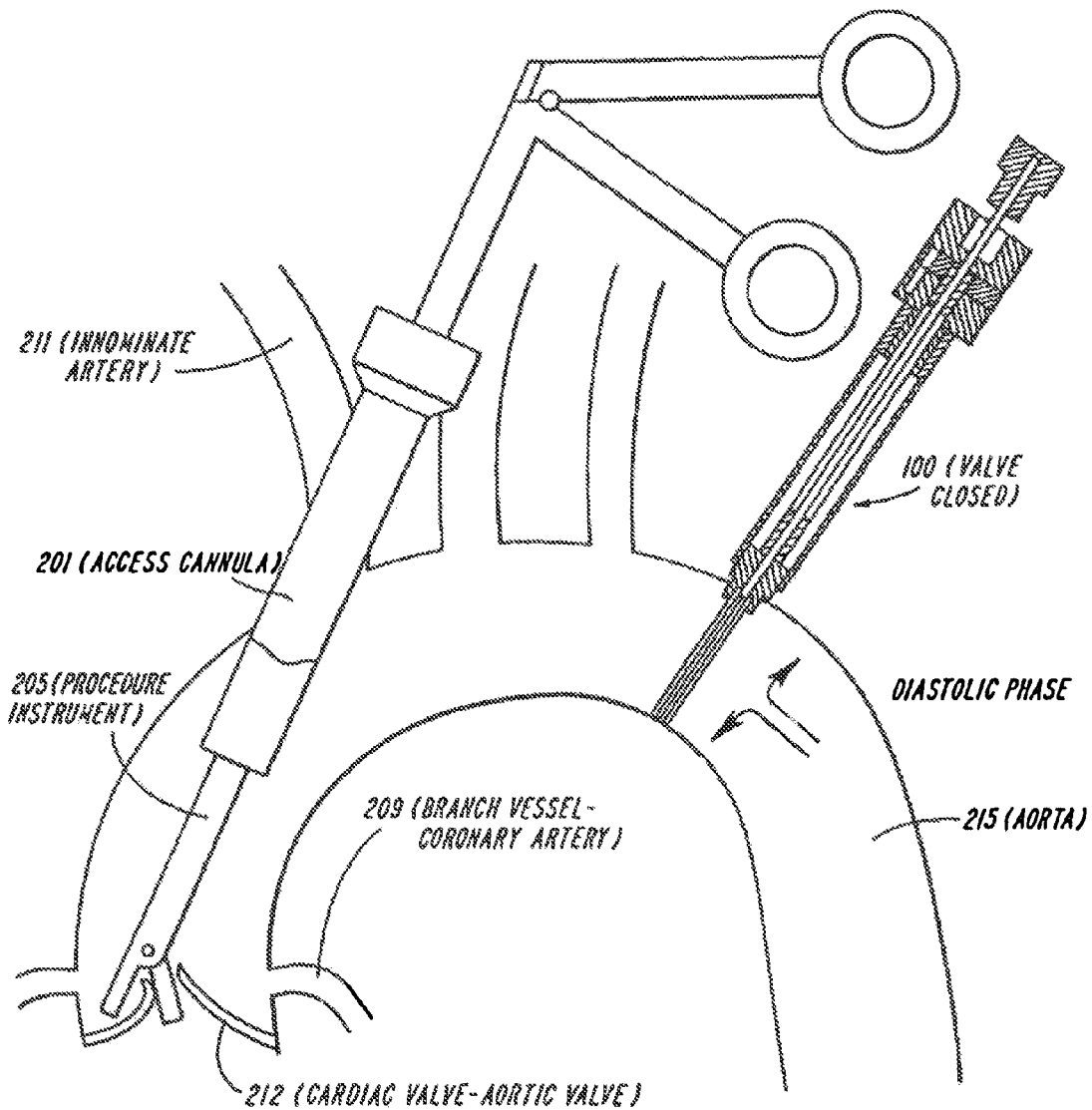
FIG. 16 depicts the temporary valve of FIG. 16 deployed in the aorta, with the valve closed.

In FIG. 16, valve assembly 100 is similarly positioned, but is closed (as in FIG. 13D'), preventing flow back toward the heart. This figure depicts the diastolic phase of cardiac rhythm. The position of valve assembly 100 distal to the three branches from the aortic arch is shown as a representative application of the device and by no means limits its application to this position.

Preferred Embodiment—Prosthetic Valve

Another aspect of the present invention is a valve fixation device, illustrated in FIGS. 17A-17E. The valve fixation device 300 is used to secure a prosthetic valve to the wall of a vessel. In a preferred embodiment, the prosthetic valve is a stentless tissue valve. The tissue valve has a base, located proximal to the heart when placed in an anatomic position, and an apex located distal to the base. The prosthetic valve preferably has three commissures and three leaflets. The apex of the commissures is toward the apex of the valve. The valve has an interior surface and an exterior surface. The interior surface serves as an attachment site for the valve leaflets to the valve anulus. The exterior of the valve is generally smooth and forms at least a portion of a cylinder. The valve has a long axis that runs along the long axis of the cylinder.

The valve fixation device consists of at least one substantially rigid strut and at least two expandable fixation rings. The strut(s) runs along the exterior surface of the valve in a direction substantially parallel to the long axis of the valve. The rings are preferably located about the circumference of the base and apex of the valve. These rings are affixed to the strut(s) such that the distance along the long axis of the valve between the rings is fixed. The rings may be located either on the interior or exterior surface of the valve. The valve is preferably affixed to both the rings and the struts by any suitable fixation means including, but not limited to barbs, sutures, staples, adhesives, or the like. In a preferred embodiment, the valve fixation device 90 has three struts 92 and two rings 91. Each of the three struts 92 is affixed to the valve along an axis that is parallel to the long axis of the valve and passes proximate to one of the valve commissures.

The rings 91 are preferably self-expanding. Alternatively, rings 91 may be plastically expandable by any suitable means, such as a balloon. The rings 91 and/or strut(s) 92 may employ barbs or spikes 83 at any location along their exterior to aid in securing the valve to the vessel wall. The rings 91 may further be affixed to the exterior of the valve and employ a sealing material 84 or other means, on rings 91, to aid in sealing rings 91 against the vessel wall.

In the preferred embodiment, the valve fixation device 90 and attached tissue valve 80 are inserted in a compressed state into the vascular system. The compressed valve/fixation system is then advanced to the site of implantation, expanded, and secured to the vessel wall. When used as an aortic valve replacement, the compressed valve/fixation system can be inserted through any peripheral artery distal to the aorta. Alternatively, the valve can be inserted through the wall of a cardiac chamber or directly into the aorta itself. Various devices can be employed to aid in delivering the valve to the implantation site, including, but not limited to delivery cannulae, catheters, and any of a variety of valve holders known in the art.

Figure 17A:
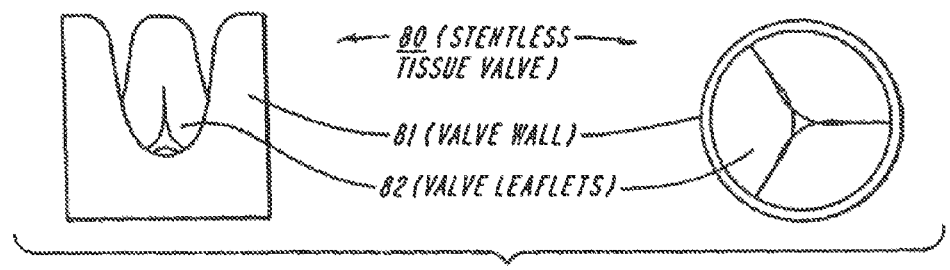
FIGS. 17A-17E show various components of a prosthetic valve and fixation system in lateral views (left side) and axial views (right side)

FIG. 17A depicts a scentless tissue valve 80 such as those known in the art. The valve consists of valve wall 81 and three attached leaflets 82. Valve wall 81 has three sections of its cylindrical form removed so as not to block branch vessels such as the coronaries. There are many variations of this type of valve prosthesis. Any flexible valve with a wall and leaflets can be used with the present invention.

Figure 17B:
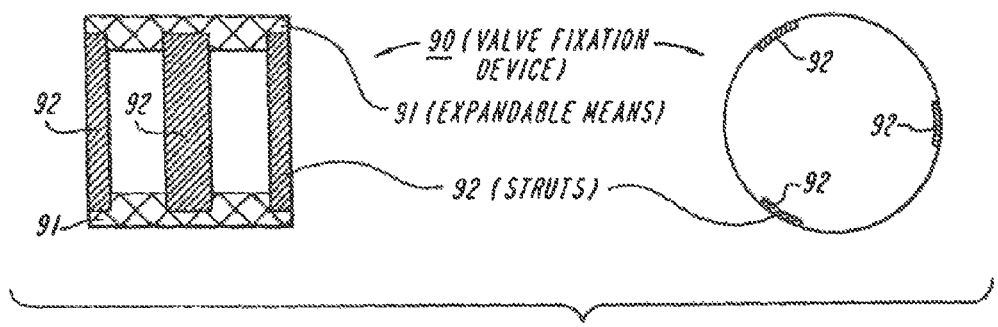

FIG. 17B depicts valve fixation device 90 of the present invention. This embodiment comprises two expandable rings-like structures 91, shown in their expanded state, and three struts 92. Struts 92 are relatively rigid and do not change dimensions from the compressed to the expanded state of the device 90. The three struts 92 are separated by roughly 120 degrees in the illustrated form, as shown in the axial view of the figure, corresponding to the three commissures of the prosthetic valve. Struts 92 are preferably relatively rigidly attached to expandable rings 91 such that the two expandable rings 91 may not rotate about their central axes relative to each other. This avoids twisting of tissue valve 80 during deployment, minimizing the risk of valve leakage.

Figure 17C:
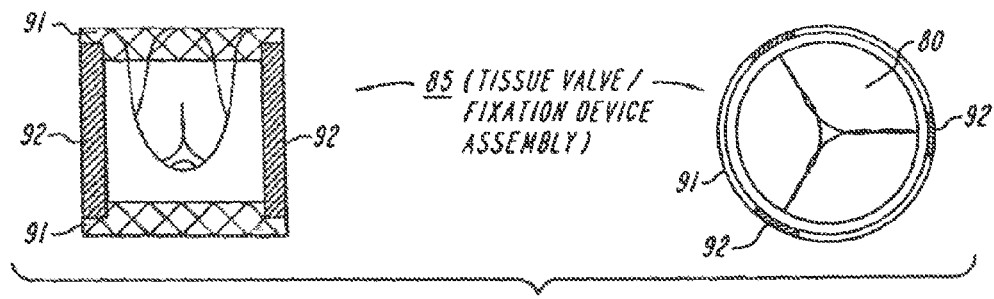

FIG. 17C depicts valve fixation device 90 affixed to tissue valve 80, forming valve assembly 85. Fixation device 90 can be affixed to tissue valve 80 at sites along struts 92, expandable rings 91, or both. In this embodiment, struts 92 and expandable rings 91 are affixed to the outside of the valve wall 81.

Figure 17D:
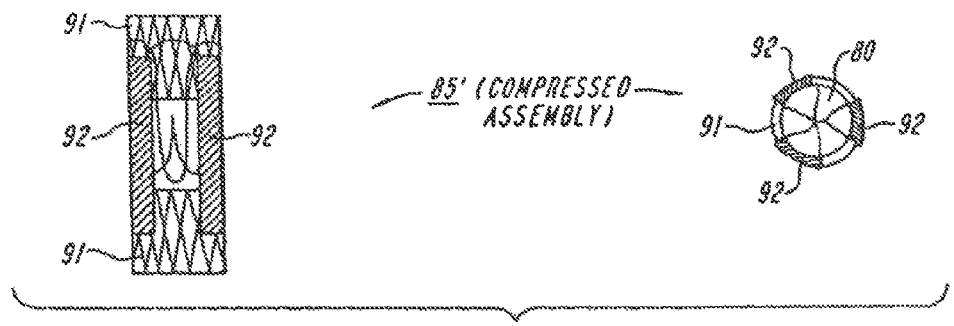

FIG. 17D depicts the assembly 85 of FIG. 17C in a compressed state 85' suitable for insertion into an artery or vein through a relative smaller opening.

Figure 17E:
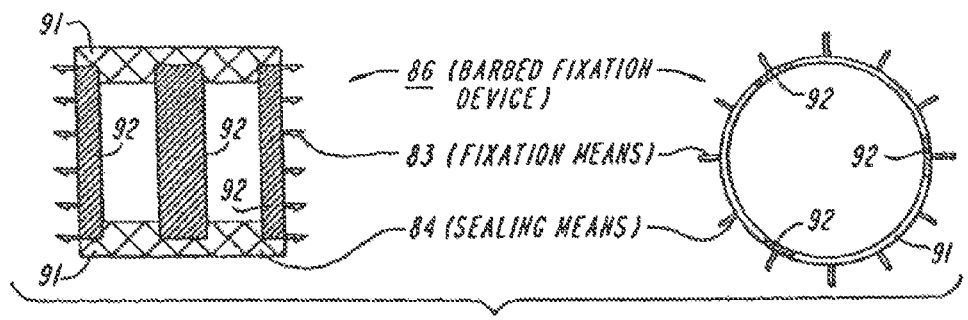

FIG. 17E depicts another embodiment of the valve fixation device 90. In embodiment 86, barbs 83 reside on the exterior surfaces of both struts 92 and expandable rings 91 to aid in securing the device 90 to a vessel wall. Felt 84 has also been added to the expandable rings 91 to aid in sealing against peri-valvular leaks. Felt 84 could be added to struts 92. Other forms of sealant may be used as well.

Preferred Embodiments—Procedure Methods

The above embodiments may be used alone or in combination with other devices to carry out procedures on a cardiac valve while the heart is beating. Below are numerous such procedure methods in accordance with the invention, which are described to clarify the breadth of possible applications of these preferred device embodiments.

Figure 18:
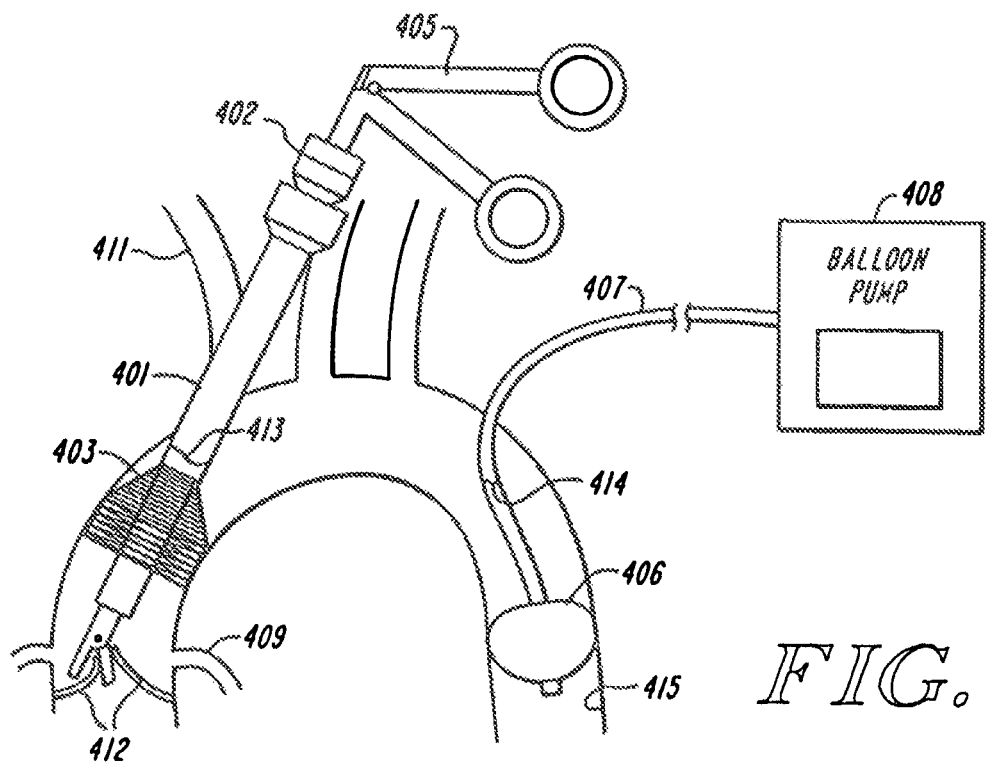
FIG. 18 depicts a method of performing surgery on a cardiac valve using a temporary valve and filter of the invention.

FIG. 18 depicts a procedure being carried out on aortic valve 412 while the heart is beating. Instrument 405 is manipulating aortic valve 412 following the placement of both temporary valve 406 and filter device 410. In this embodiment, temporary valve 406 and filter device 401 (for example device 10 of FIGS. 1A-1F) are separate instruments that have been inserted directly into the aorta through separate insertion sites 414 and 413. Alternatively, valve 406 and filter 410 may be effected in a single instrument placed through a single incision. Valve 406 and filter 410 may also be inserted from a peripheral vessel and advanced to a location within the aorta.

Mesh filter 403 is deployed through outer cannula 401 to a preferred site proximal to the brachiocephalic artery 411. In this position, filter 403 prevents distal embolization of debris that may be dislodged during manipulation of valve 412. Portions of inner and outer cannulae 401 and 402 and instrument 405 extend to the exterior of the aorta where they can be manipulated by a surgeon. In the method illustrated by FIG. 18, balloon valve 406 is deployed in the descending aorta 415. Balloon 406 is inflated and deflated by an attached balloon pump 408 exterior to the patient. Balloon pump 408 is in fluid connection with balloon 406 through tube 407. Balloon pump 408 is timed to the cardiac rhythm so that it inflates balloon 406 during substantially all of the diastolic phase and deflates balloon 406 during substantially all of the systolic phase. This allows the valve 406 to perform the function of aortic valve 412 while the aortic valve is manipulated.

Figure 19:
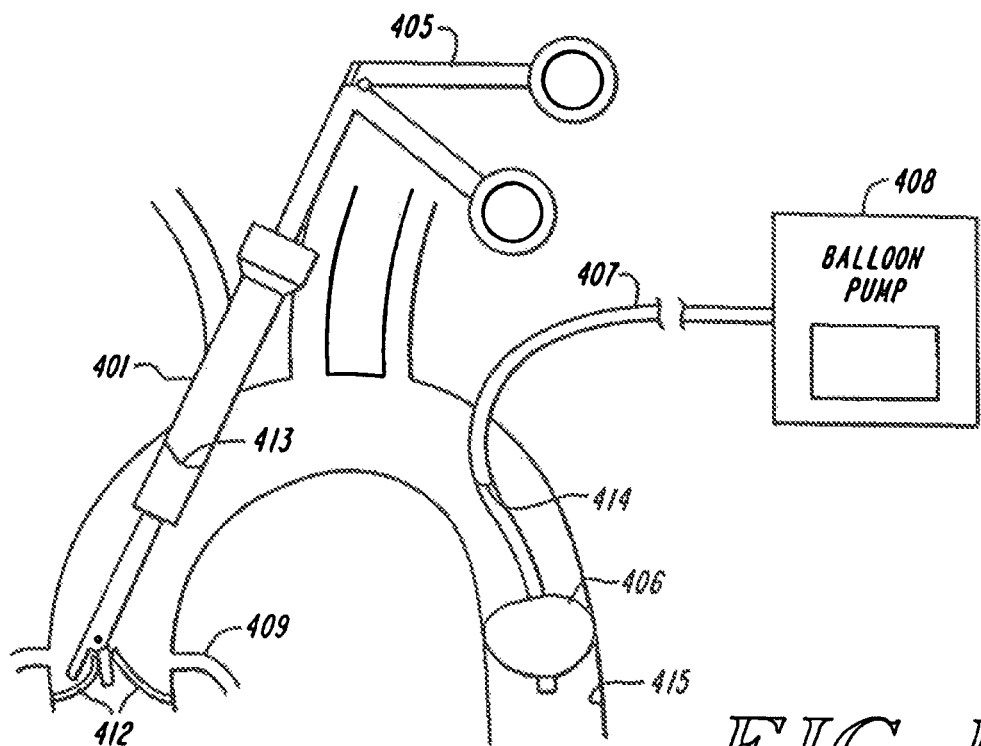
FIG. 19 depicts another method of performing surgery on a cardiac valve using a temporary valve of the invention.
Figure 20:
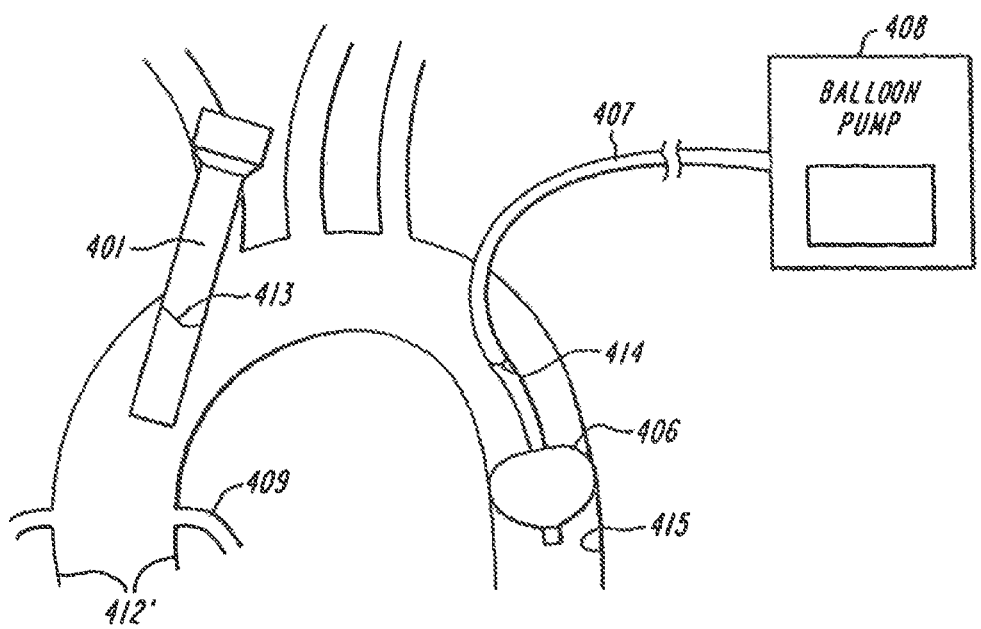
FIG. 20 depicts the methods of FIGS. 18 and 19 following removal of the cardiac valve and inner cannula.
Figure 21:
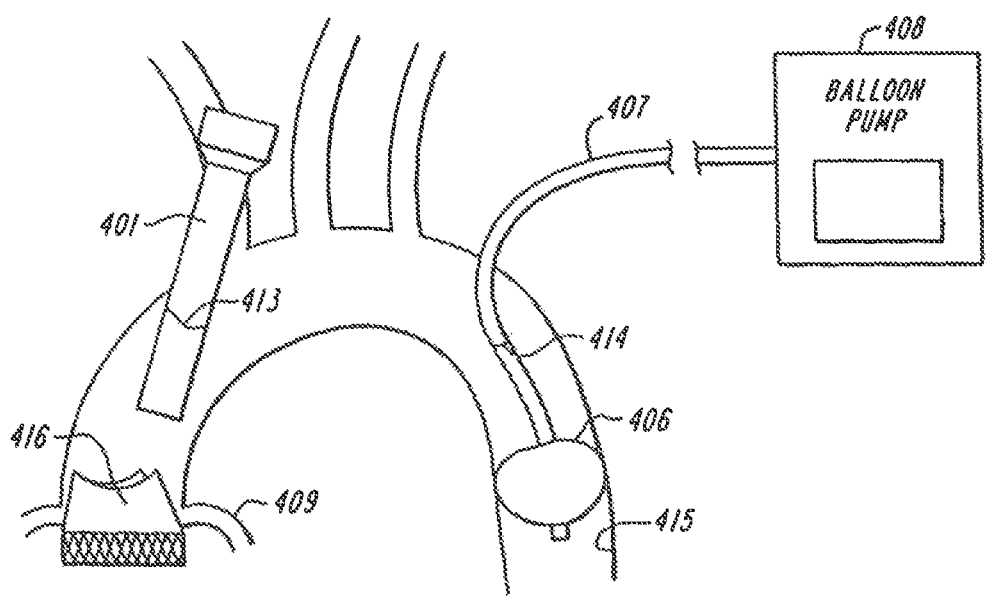
FIG. 21 depicts deployment of an expandable prosthetic valve through the outer cannula and into the valve annulus, in accordance with the invention.

FIGS. 19, 20, and 21 show another form of the present invention. Those figures depict sequential views of method of removing the native aortic valve and replacing it with a permanent prosthetic valve while the heart is beating. In FIG. 19, balloon valve 406 has been placed in the descending aorta 415. Cannula 401 has been placed into the aorta to allow the passage of instrument 405. Cannula 401 may have a valve (not shown) along its interior that acts to prevent the flow of blood through the cannula while allowing the passage of various instruments. Instrument 405 has been inserted through cannula 401 to remove native aortic valve 412. FIG. 20 shows the embodiment described in FIG. 19 after substantially all of the aortic valve has been removed. Portions 412' of the aortic valve may remain without deviating from the scope of this invention. Indeed resection of native valve 412 can be limited to removal of those portions of the right and left valve leaflets that would cover coronary arteries 409 if the valve were to be compressed against the inner walls of the aorta. Instrument 405 has been withdrawn from outer cannula 401 to allow the insertion of valve prosthesis 416 into the aorta. In this figure, temporary valve 406 is performing the full function of the resected aortic valve. FIG. 21 shows valve prosthesis 416 expanded against and affixed to the aortic wall at a site near the previous attachment of the native valve. Once valve prosthesis 416 is in place and functioning, temporary valve 406 can be removed. No filter is shown in FIGS. 19, 20, and 21. A filter is not necessary for completing the procedure, but could be used without deviating from the intent of the present invention.

Another method of replacing a cardiac valve while the heart is beating, employs described using a combination of the methods disclosed in FIGS. 18, 20, and 21. In accordance with the latter method, a set of two concentric cannulae, inner cannula 402 that fits within the lumen of outer cannula 401, are inserted into the vessel. The method further involves the steps of advancing the set of cannulae to a site downstream of the cardiac valve, expanding an expandable member 403 from the exterior of the inner cannula 402, performing a procedure at least in part through the lumen of the inner cannula that removes or disrupts cardiac valve 412, retracting inner cannula 402 and expandable member 403 through the inner lumen of outer cannula 401, leaving the distal end of outer cannula 401 near the annulus of cardiac valve 412, inserting a compressed valve prosthesis 416 through the inner lumen of outer cannula 401 to the site of the cardiac valve anulus, and expanding and affixing prosthetic valve 416 to the cardiac valve annulus. Using the set of two cannulae allows the insertion and removal of expandable member 403 on the exterior of inner cannula 402 as well as valve prosthesis 416 and other instruments through the lumen of outer cannula 401 without losing the position of outer cannula 401 relative to the cardiac valve during the procedure. Expandable member 403 is located anywhere along the length of inner cannula 402 and performs any number of functions such as acting as a temporary valve, acting as a filter, or removing or disrupting the cardiac valve leaflets.

Figure 22:
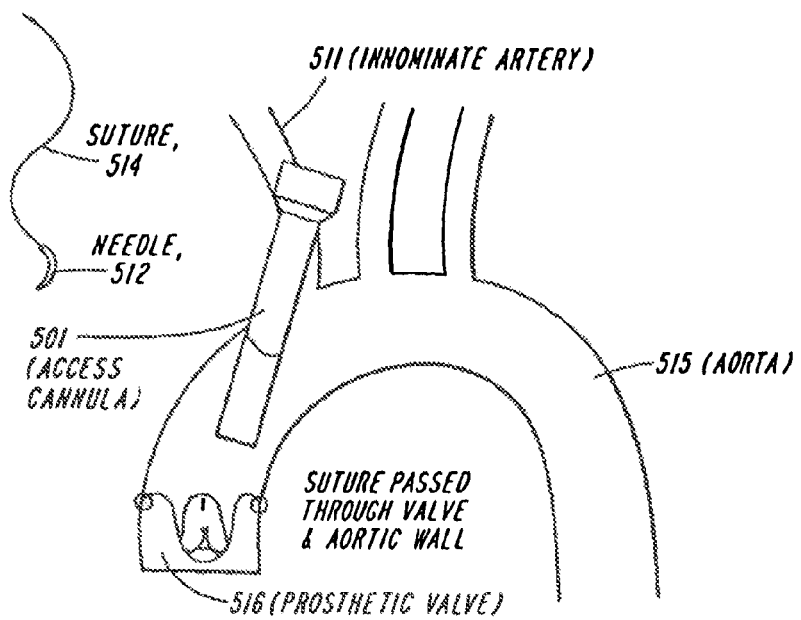
FIG. 22 depicts an exemplary method of fixing a prosthetic valve to a vessel wall during cardiac rhythm, in accordance with the invention.

FIG. 22 depicts one method of fixing a prosthetic valve 516 to a vessel wall during cardiac rhythm. In this embodiment, prosthetic valve 516 is inserted into aorta 515 in a compressed state through access cannula 501. Prosthetic valve 516 is then expanded to abut the inner wall of aorta 515. A needle 512 and suture 514 are then passed from the outer surface of aorta 515 through the aortic wall and into the prosthetic valve 516. In this depiction, three sutures are used to tack prosthetic valve 516 to the aortic wall in locations superior to the valve commissures. Alternatively, a fixation means can be passed from the interior wall of aorta 515 through to the exterior surface. The fixation means can be a staple, suture or other suitable means.

In accordance with another aspect of the present invention, a compressed prosthetic valve is inserted into a vessel downstream of the cardiac valve to be replaced. The prosthetic valve is then expanded to allow it to function temporarily in its downstream location. With that valve temporarily placed, and functioning, a procedure on the cardiac valve is performed, involving the disruption and/or removal of the cardiac valve. Then the prosthetic valve is advanced toward the site of the excised or disrupted cardiac valve, and affixed at a site within the vessel at or near the site of the excised or disrupted cardiac valve. During the procedure on the cardiac valve, the expanded prosthetic valve functions as the native valve, preventing retrograde flow.

The cardiac valve procedure occurring while the prosthetic valve is downstream of its final position, may be performed through an incision somewhere between the cardiac valve and the prosthetic valve. Alternatively, the procedure could be done with tools inserted through the functioning prosthetic.

Figure 23A:
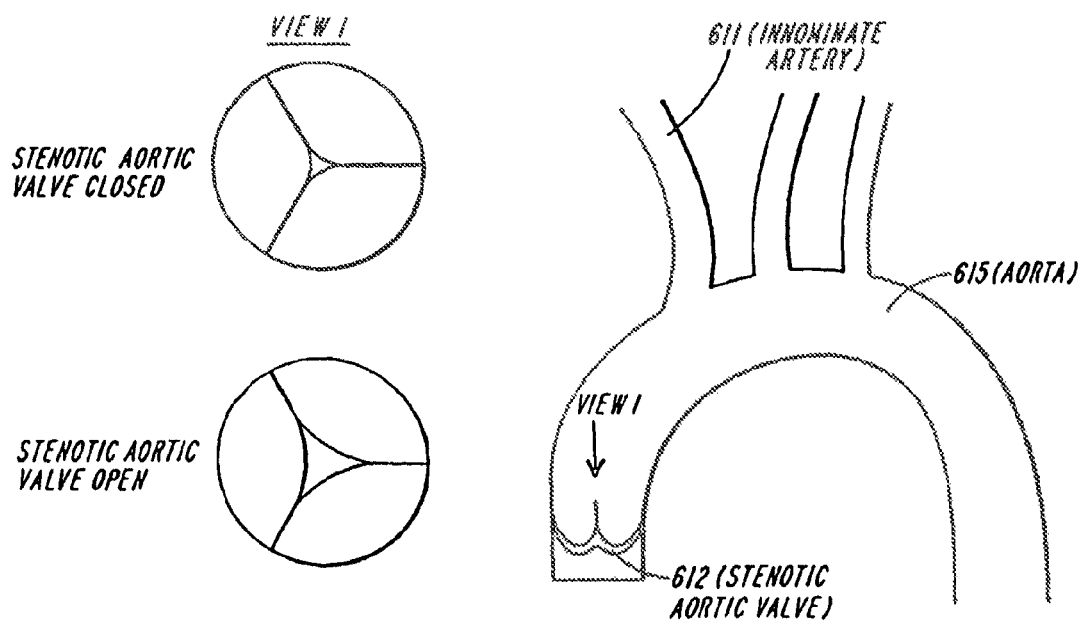

FIGS. 23A and 23B depict a method for repairing a stenotic aortic valve in accordance with the invention. FIG. 23A shows stenotic aortic valve 612 within the aortic root. View 1 in this figure shows two views of stenotic valve 612 looking along the long axis of aorta 615 proximal to the valve. In this view, the leaflets of valve 612 provide a reduced aperture due to the stenosis.

FIG. 23B shows the aortic valve after the repair method of the invention has been implemented. Initially, the aortic valve 612" is disrupted by incising each leaflet such that six leaflets are formed. A balloon valvuloplasty may optionally be performed on valve 612". Following the disruption of valve 612", a valve support 620 is positioned upstream of the valve 612". Preferably, the valve support 620 includes an expandable outer ring (circular or otherwise, eg elliptical, oval, polygonal), which is spanned by a bloodflow permeable structure. The outer ring is expanded to be proximal to and affixed to the aortic wall, so that the support structure provides a surface against which the disrupted leaflets can collapse, forming a multileafed flap valve, similar to the valve described above in conjunction with FIGS. 12-14.

Figure 24:
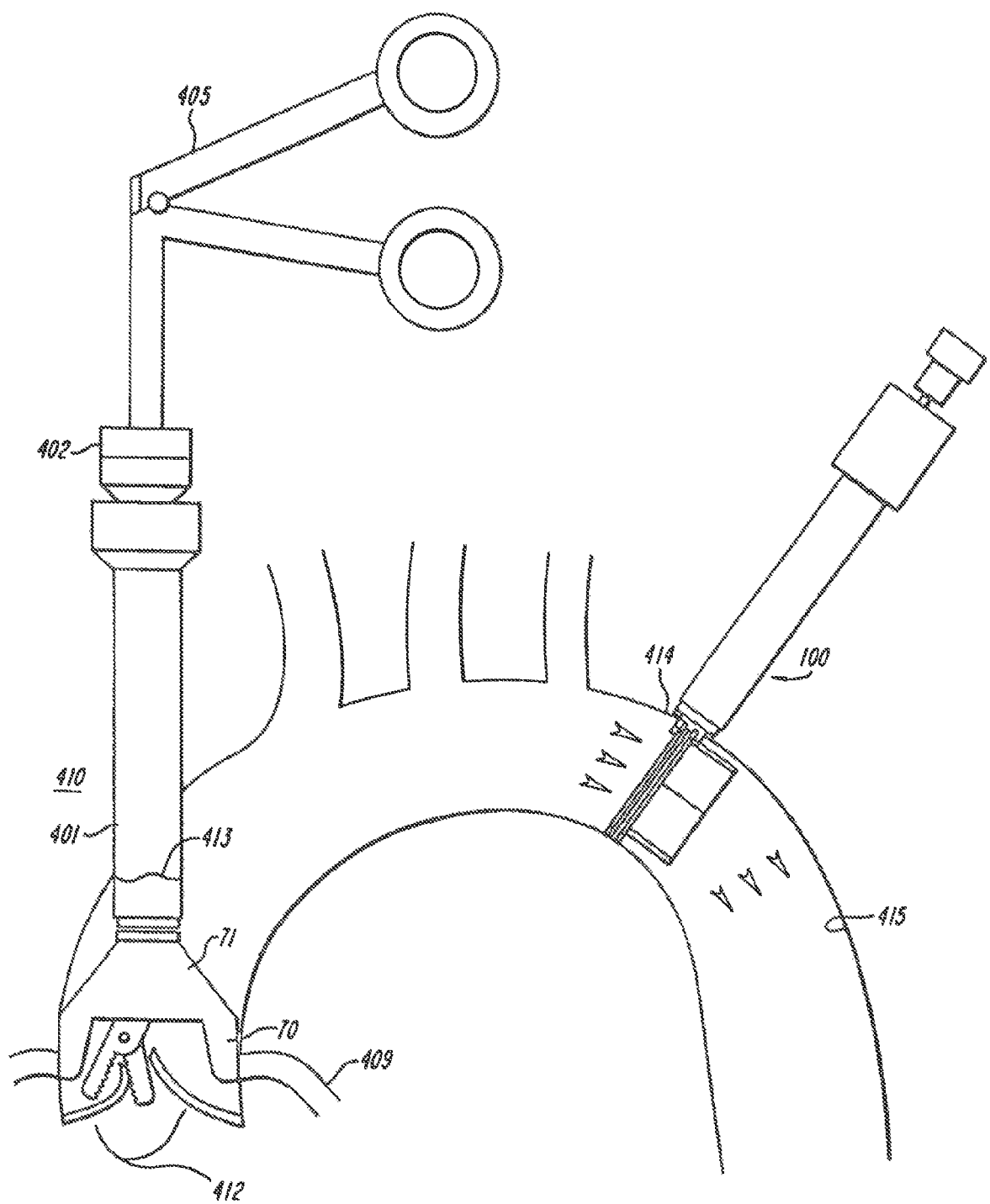
FIG. 24 depicts another method for performing surgery in a cardiac valve using a temporary valve and filter in accordance with the invention.

FIG. 24 depicts a procedure being performed on the aortic valve 412 while the heart is beating. Instrument 405 is manipulating aortic valve 412 following the placement of both temporary valve 100 and filter device 410 (for example, device 10 of FIG. 1F). In this embodiment, temporary valve 100 and filter device 410 have been inserted directly into the aorta through separate insertion sites 414 and 413.

Mesh filter (not visible) has been deployed through outer cannula 401 to a site proximal to the coronary arteries 409. Filter material 71 covers the mesh filter. Filter extensions 70 extend from the filter material and form filter leaflets that prevent embolic material from entering the coronary arteries 409. Portions of the inner and outer cannulae 401 and 402 and instruments 405 extend to the exterior of the aorta where they can be manipulated by the surgeon.

In the method illustrated in FIG. 24, temporary valve 100 is deployed in the descending aorta 415, and as described earlier, expands to occupy the entire flow path. Temporary valve 100 is shown in the systolic phase of cardiac rhythm, i.e. with its valve open (as in FIG. 13D'), allowing flow through the device.

In other embodiments of the invention the temporary valve and/or filter may be deployed downstream of the aortic valve, or in still other forms, downstream of the mitral or other cardiac valves. Further, these devices may be deployed downstream of one cardiac valve while procedures are being performed on another cardiac valve upstream of the devices.

Although preferred and other embodiments of the invention are described herein, further embodiments may be perceived by those skilled in the art without departing from the scope of the claims.

The invention claimed is:

1. A method of performing an endovascular procedure within a patient, the method comprising:
    inserting a filter into the patient's vascular system to restrict the passage of emboli through the filter while allowing blood to flow through the filter;
    inserting a prosthetic valve into the patient's vascular system in a compressed state;
    advancing the prosthetic valve to a site of implantation upstream of the filter;
    implanting the prosthetic valve at the site of implantation by expanding at least a portion of the prosthetic valve; and
    removing the filter from the patient's vascular system, wherein the prosthetic valve remains implanted at the site of implantation.

2. The method of claim 1 further comprising inserting the filter into the aorta.

3. The method of claim 1 further comprising inserting the filter into a peripheral artery.

4. The method of claim 3 further comprising advancing the filter into the aorta.

5. The method of claim 1 further comprising inserting the filter into the vascular system in a compressed state.

6. The method of claim 1 further comprising expanding the filter to a larger state at a desired site within the vascular system.

7. The method of claim 1 wherein at least a portion of the filter self-expands.

8. The method of claim 1 wherein at least a portion of the filter is expandable.

9. The method of claim 1 wherein at least a portion of the filter is positioned in the vascular system upstream of a branch artery.

10. The method of claim 1 wherein the branch artery is the patient's braciolcephalic artery.

11. The method of claim 1 wherein the filter is inserted and removed from the patient's vascular system via a catheter device.

12. The method of claim 1 wherein the filter is inserted and removed from the patient's vascular system via a cannula device.

13. The method of claim 1 wherein the filter prevents one or more emboli from reaching the patient's brain.

14. The method of claim 1 wherein the filter comprises a mesh material.

15. The method of claim 1 wherein the filter comprises a selectively permeable membrane material.

16. The method of claim 1 wherein the procedure is a beating heart procedure.

17. The method of claim 1 wherein the procedure is not a cardiac arrest or cardiac bypass procedure.

18. The method of claim 1 further comprising placing at least a portion of the filter over the ostium of one or more arteries.

19. The method of claim 1 further comprising placing at least a portion of the filter over the ostium of one or more arteries that branch from the aorta.

20. The method of claim 1 further comprising inserting the prosthetic valve into the vascular system via a catheter device.

21. The method of claim 1 further comprising inserting the prosthetic valve into the vascular system via a cannula device.

22. The method of claim 1 wherein the site of implantation is a cardiac valve site.

23. The method of claim 1 wherein the site of implantation is a cardiac valve annulus.

24. The method of claim 1 wherein the site of implantation is upstream of a cardiac valve.

25. The method of claim 1 wherein the site of implantation is downstream from a cardiac valve.

26. The method of claim 1 wherein the site of implantation is an aortic valve.

27. The method of claim 1 wherein at least a portion of the prosthetic valve is self-expanding.

28. The method of claim 1 wherein at least a portion of the prosthetic valve is expandable.

29. The method of claim 1 wherein at least a portion of the prosthetic valve is expanded via a balloon.

30. The method of claim 1 further comprising inserting the prosthetic valve into the vascular system through a peripheral artery.

31. The method of claim 1 further comprising inserting the prosthetic valve into the vascular system through a wall of a cardiac chamber.

32. The method of claim 1 further comprising inserting the prosthetic valve into the vascular system through a wall of the patient's aorta.

33. A method of performing an endovascular procedure within a patient, the method comprising:
inserting a compressed filter into the patient's vascular system;
expanding the filter within the vascular system downstream of a cardiac valve, the filter restricting the passage of emboli through the filter while allowing blood to flow through the filter;
inserting a compressed prosthetic valve into the vascular system;
expanding the prosthetic valve within the vascular system upstream of the filter; and
removing the filter from the vascular system, wherein the prosthetic valve remains expanded within the vascular system.

34. A method of performing an endovascular procedure within a patient, the method comprising:
inserting a compressed filter into the vascular system of the patient;
expanding the filter within the patient's aorta downstream of a cardiac valve, the expanded filter restricting the passage of emboli into one or more arteries that branch from the aorta;
inserting a compressed prosthetic valve into the vascular system of the patient;
expanding the prosthetic valve within at least a portion of the cardiac valve; and
removing the filter from the vascular system, wherein the prosthetic valve remains expanded within at least the portion of the cardiac valve.

* * * * *